(12) United States Patent
Howsham et al.

(10) Patent No.: US 8,809,340 B2
(45) Date of Patent: Aug. 19, 2014

(54) CRYSTALLINE FORM

(71) Applicants: Catherine Howsham, Horsham (GB); Christian Lindenberg, Basel (CH); Anett Perlberg, Gunzgen (CH); Nicola Tufilli, Moehlin (CH)

(72) Inventors: Catherine Howsham, Horsham (GB); Christian Lindenberg, Basel (CH); Anett Perlberg, Gunzgen (CH); Nicola Tufilli, Moehlin (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 13/797,411

(22) Filed: Mar. 12, 2013

(65) Prior Publication Data

US 2013/0345239 A1    Dec. 26, 2013

Related U.S. Application Data

(60) Provisional application No. 61/612,727, filed on Mar. 19, 2012.

(51) Int. Cl.
  *A61K 31/4965* (2006.01)
  *C07D 241/02* (2006.01)

(52) U.S. Cl.
  USPC .................. 514/255.05; 514/255.06; 544/407

(58) Field of Classification Search
  USPC .................. 514/255.05, 255.06; 544/407
  See application file for complete search history.

(56) References Cited

FOREIGN PATENT DOCUMENTS

| WO | WO 2009/074575 | 6/2009 |
|---|---|---|
| WO | WO 2009/150137 | 12/2009 |
| WO | WO 2011/050325 | 4/2011 |
| WO | WO 2012/035158 | 3/2012 |

OTHER PUBLICATIONS

Jack H. Li et al., "Stereoselective Blockade of Amphibian Epithelial Sodium Channels by Amiloride Analogs" *Journal Pharmacology and Experimental Therapeutics* 267(3):1081-1084, 1993.

*Primary Examiner* — Raymond Henley, III
(74) *Attorney, Agent, or Firm* — Qian Zhang

(57) ABSTRACT

This invention relates to a new crystalline form of the succinate salt of the epithelial sodium channel (ENaC) blocker 3-(3-{2-[(E)-3,5-Diamino-6-chloro-pyrazine-2-carbonylimino]-1,3,8-triaza-spiro[4.5]decane-8-carbonyl}-benzenesulfonylamino)-propionic acid dipropylcarbamoylmethyl ester, pharmaceutical compositions comprising said crystalline form, uses of said crystalline form and pharmaceutical compositions, and methods for preparing said crystalline form.

13 Claims, 11 Drawing Sheets

CRYSTALLINE FORM

CROSS-REFERENCE TO RELATED APPLICATION

This application claims the benefit of priority to U.S. Provisional Application Ser. No. 61/612,727, filed on Mar. 19, 2012, which is incorporated herein by reference in its entirety.

TECHNICAL FIELD

This invention relates to a new crystalline form of the succinate salt of the epithelial sodium channel (ENaC) blocker 3-(3-{2-[(E)-3,5-Diamino-6-chloro-pyrazine-2-carbonylimino]-1,3,8-triaza-spiro[4.5]decane-8-carbonyl}-benzenesulfonylamino)-propionic acid dipropylcarbamoylmethyl ester, pharmaceutical compositions comprising said crystalline form, uses of said crystalline form and pharmaceutical compositions, and methods for preparing said crystalline form.

BACKGROUND

International patent application publication WO 2012/035158 (PCT/EP2011/066151) discloses methods for preparing the ENaC blocker 3-(3-{2-[(E)-3,5-Diamino-6-chloro-pyrazine-2-carbonylimino]-1,3,8-triaza-spiro[4.5]decane-8-carbonyl}-benzenesulfonylamino)-propionic acid dipropylcarbamoylmethyl ester and its succinate salt.

Diseases mediated by blockade of the epithelial sodium channel, include diseases associated with the regulation of fluid volumes across epithelial membranes. For example, the volume of airway surface liquid is a key regulator of mucociliary clearance and the maintenance of lung health. The blockade of the epithelial sodium channel will promote fluid accumulation on the mucosal side of the airway epithelium thereby promoting mucus clearance and preventing the accumulation of mucus and sputum in respiratory tissues (including lung airways). Such diseases include respiratory diseases, such as cystic fibrosis, primary ciliary dyskinesia, chronic bronchitis, chronic obstructive pulmonary disease (COPD), asthma, respiratory tract infections (acute and chronic; viral and bacterial) and lung carcinoma. Diseases mediated by blockade of the epithelial sodium channel also include diseases other than respiratory diseases that are associated with abnormal fluid regulation across an epithelium, perhaps involving abnormal physiology of the protective surface liquids on their surface, e.g., xerostomia (dry mouth) or keratoconjunctivitis sire (dry eye). Furthermore, blockade of the epithelial sodium channel in the kidney could be used to promote diuresis and thereby induce a hypotensive effect.

DESCRIPTION OF THE EMBODIMENTS

Three polymorphic forms (Form A, B and C) of the succinate salt of ENaC blocker 3-(3-{2-[(E)-3,5-Diamino-6-chloro-pyrazine-2-carbonylimino]-1,3,8-triaza-spiro[4.5]decane-8-carbonyl}-benzenesulfonylamino)-propionic acid dipropylcarbamoylmethyl ester (3-(3-{2-[(E)-3,5-Diamino-6-chloro-pyrazine-2-carbonylimino]-1,3,8-triaza-spiro[4.5]decane-8-carbonyl}-benzenesulfonylamino)-propionic acid dipropylcarbamoylmethyl ester:succinic acid=1:1) are disclosed. Methods for preparing Form A and B have been described in international patent application publication WO 2012/035158 (PCT/EP2011/066151).

Hence, in a first aspect, the present invention provides a crystalline form of 3-(3-{2-[(E)-3,5-Diamino-6-chloro-pyrazine-2-carbonylimino]-1,3,8-triaza-spiro[4.5]decane-8-carbonyl}-benzenesulfonylamino)-propionic acid dipropylcarbamoylmethyl ester succinate of formula

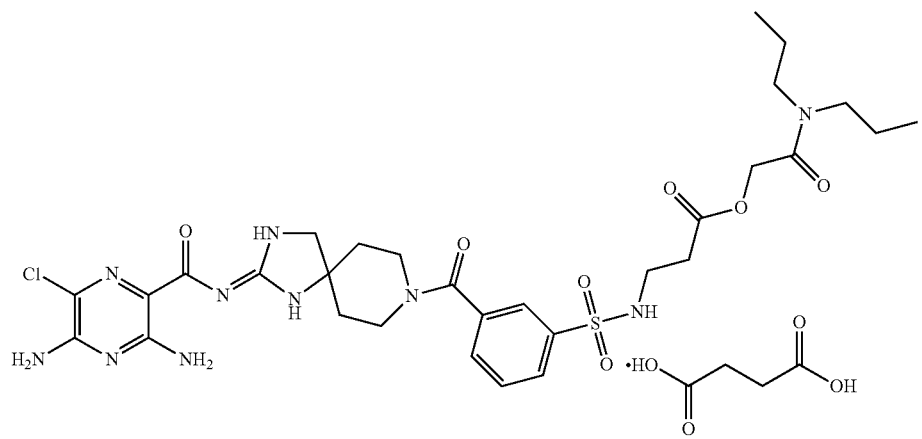

comprising Form C.

In one embodiment of the first aspect, the crystalline form consists essentially of Form C.

In another embodiment of the first aspect, the crystalline form comprises Form C wherein said Form C is in substantially pure form.

In another embodiment of the first aspect, the crystalline form is characterized by an x-ray powder diffraction pattern comprising four or more 2-theta values selected from the group of 7.0°±0.2, 10.6°±0.2, 14.3°±0.2, 18.2°±0.2, 18.6°±0.2, 19.2°±0.2, 21.2°±0.2, 21.8°±0.2, 24.7°±0.2, 29.0°±0.2 and 31.5°±0.2 at a temperature of 21-26° C. ° C.

In another embodiment of the first aspect, the crystalline form is characterized by an x-ray powder diffraction pattern comprising six or more 2-theta values selected from the group of 7.0°±0.2, 10.6°±0.2, 14.3°±0.2, 18.2°±0.2, 18.6°±0.2, 19.2°±0.2, 21.2°±0.2, 21.8°±0.2, 24.7°±0.2, 29.0°±0.2 and 31.5°±0.2 at a temperature of 21-26° C. ° C.

Figure 7:
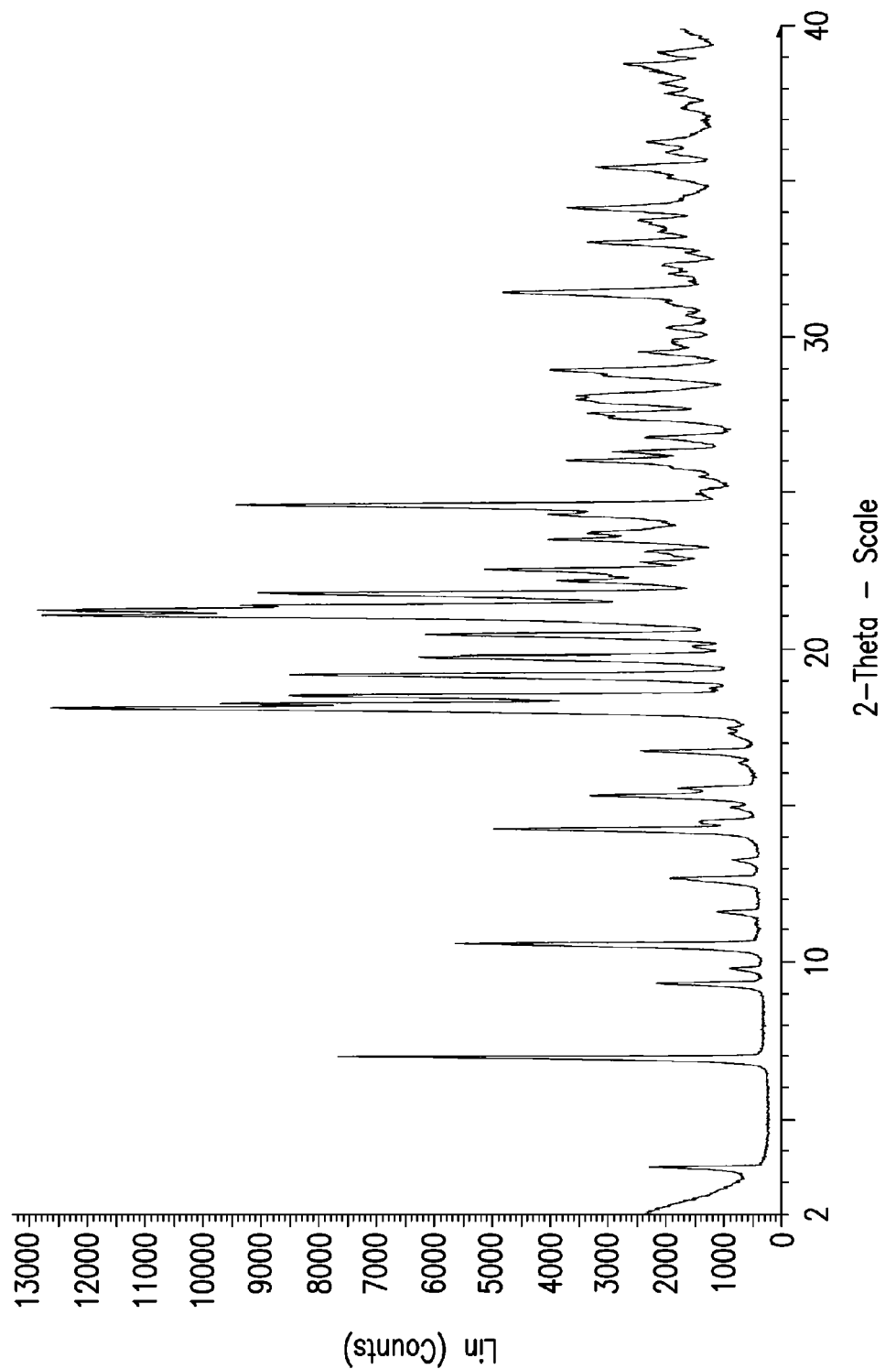
FIG. 7 shows the x-ray powder diffraction pattern recorded for Form C (Example 10) and was recorded on a Bruker™ D8 diffractometer using CuKα radiation (λ=1.5418 Å).

In another embodiment of the first aspect, the crystalline form has an x-ray powder diffraction spectrum which is substantially the same as the x-ray powder diffraction spectrum shown in FIG. 7.

Figure 8:
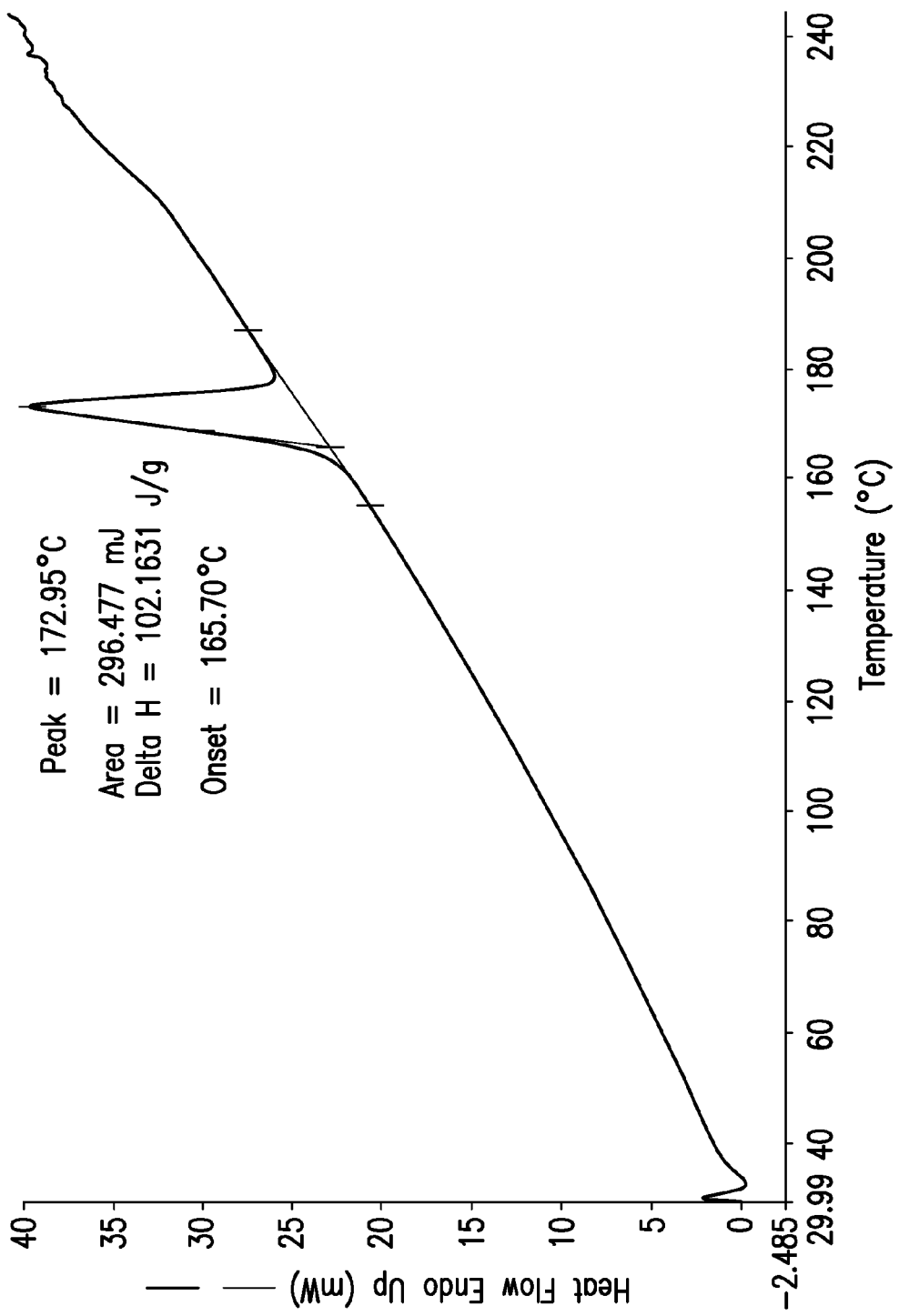
FIG. 8 shows the differential scanning calorimetry (DSC) trace of Form C (Example 10) and was recorded on a Perkin Elmer Diamond DSC instrument with aluminium pan (Perkin Elmer, type BO14-3018); heating rate 20 K/min, temperature range: 30 to 250° C.

In another embodiment of the first aspect, the crystalline form has a differential scanning calorimetry thermogram which is substantially the same as that shown in FIG. 8.

As used herein, the term "substantially pure" with reference to a particular polymorphic form means that the polymorphic form includes less than 10%, preferably less than 5%, more preferably less than 3%, most preferably less than 1% by weight of any other physical forms (polymorphs) of the compound.

As used herein "polymorph" refers to crystalline forms having the same chemical composition but different spatial arrangements of the molecules, atoms, and/or ions forming the crystal.

Throughout this specification and in the claims that follow, unless the context requires otherwise, the word "comprise", or variations such as "comprises" or "comprising", should be understood to imply the inclusion of a stated integer or step or group of integers or steps but not the exclusion of any other integer or step or group of integers or steps.

As used herein, the term "crystalline form of the invention" refers to the crystalline form as defined in the first aspect or any embodiment of the first aspect.

In a second aspect, there is provided a pharmaceutical composition comprising the crystalline form according to the first aspect or any embodiments of the first aspect and a pharmaceutically acceptable carrier or diluent.

In an embodiment of the second aspect, wherein Form C is in substantially pure form.

In another embodiment of the second aspect, the pharmaceutical composition is in inhalable form.

In a third aspect, there is provided a pharmaceutical composition according to the second aspect or an embodiment of the second aspect in combination with one or more additional active ingredients.

In a fourth aspect, there is provided a crystalline form according to the first aspect or any embodiment of the first aspect and a pharmaceutical composition according to the second aspect or any embodiment of the second aspect for use in the treatment of respiratory diseases, such as cystic fibrosis, primary ciliary dyskinesia, chronic bronchitis, chronic obstructive pulmonary disease (COPD), asthma, respiratory tract infections (acute and chronic; viral and bacterial) and lung carcinoma.

In a fifth aspect, there is provided the use of a crystalline form according to the first aspect or any embodiment of the first aspect or of a composition according to the second aspect or any embodiment of the second aspect in the manufacture of a medicament for the treatment of respiratory diseases, such as cystic fibrosis, primary ciliary dyskinesia, chronic bronchitis, chronic obstructive pulmonary disease (COPD), asthma, respiratory tract infections (acute and chronic; viral and bacterial) and lung carcinoma.

In a sixth aspect, there is provided a method of treating respiratory diseases, such as cystic fibrosis, primary ciliary dyskinesia, chronic bronchitis, chronic obstructive pulmonary disease (COPD), asthma, respiratory tract infections (acute and chronic; viral and bacterial) and lung carcinoma comprising administering to a patient in need thereof an effective amount of a crystalline form according to the first aspect or any embodiment of the first aspect or of a pharmaceutical composition according to the second aspect or any embodiment of the second aspect.

In a seventh aspect, there is provided an inhalation device that contains and is adapted to deliver a crystalline form according to the first aspect or any embodiment of the first aspect by pulmonary administration. In certain preferred embodiments the inhalation device is a dry powder inhaler, for example the BREEZHALER® inhalation device.

Novel polymorphic Form C of 3-(3-{2-[(E)-3,5-Diamino-6-chloro-pyrazine-2-carbonylimino]-1,3,8-triaza-spiro[4.5] decane-8-carbonyl}-benzenesulfonylamino)-propionic acid dipropylcarbamoylmethyl ester succinate has been shown to be thermodynamically more stable than Form A.

Form B is a group of isomorphous solvates that appear as a transient crystalline form in suspension during the crystallization of Form A. Form B transforms into Form A upon drying.

The agents of the invention may be administered by any appropriate route, e.g. orally, for example in the form of a tablet or capsule; parenterally, for example intravenously; topically to the skin; intranasally, for example in the treatment of allergic rhinitis; or, preferably, by inhalation, particularly in the treatment of obstructive or inflammatory airways diseases. In particular, the agents of the invention may be delivered as an inhalable formulation for the treatment of COPD, cystic fibrosis or asthma.

The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc.

Typically, the pharmaceutical compositions are tablets or gelatin capsules comprising the active ingredient together with a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and/or e) absorbents, colorants, flavors and sweeteners.

Tablets may be either film coated or enteric coated according to methods known in the art.

Suitable compositions for oral administration include an effective amount of the crystalline form of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of the crystalline form of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

Where the inhalable form of the active ingredient is an aerosol composition, the inhalation device may be an aerosol vial provided with a valve adapted to deliver a metered dose, such as 10 to 100 µl, e.g. 25 to 50 µl, of the composition, i.e. a device known as a metered dose inhaler. Suitable such aerosol vials and procedures for containing within them aerosol compositions under pressure are well known to those skilled in the art of inhalation therapy. For example, an aerosol composition may be administered from a coated can, for example as described in EP-A-0642992. Where the inhalable form of the active ingredient is a nebulizable aqueous, organic or aqueous/organic dispersion, the inhalation device may be a known nebulizer, for example a conventional pneumatic nebulizer such as an airjet nebulizer, or an ultrasonic nebulizer, which may contain, for example, from 1 to 50 ml, commonly 1 to 10 ml, of the dispersion; or a hand-held nebulizer, sometimes referred to as a soft mist or soft spray inhaler, for example an electronically controlled device such as an AERx (Aradigm, US) or Aerodose (Aerogen), or a mechanical device such as a RESPIMAT (Boehringer Ingelheim) nebulizer which allows much smaller nebulized volumes, e.g. 10 to 100 μl, than conventional nebulizers. Where the inhalable form of the active ingredient is the finely divided particulate form, the inhalation device may be, for example, a dry powder inhalation device adapted to deliver dry powder from a capsule or blister containing a dry powder comprising a dosage unit of (A) and/or (B) or a multidose dry powder inhalation (MDPI) device adapted to deliver, for example, 3-25 mg of dry powder comprising a dosage unit of (A) and/or (B) per actuation. The dry powder composition preferably contains a diluent or carrier, such as lactose, and a compound that helps to protect against product performance deterioration due to moisture e.g. magnesium stearate. Suitable such dry powder inhalation devices include devices disclosed in U.S. Pat. No. 3,991,761 (including the AEROLIZER™ device), WO 05/113042 (including the BREEZHALER™ device), WO 97/20589 (including the CERTIHALER™ device), WO 97/30743 (including the TWISTHALER™ device), WO 05/37353 (including the GYROHALER™ device), U.S. Pat. No. 6,536,427 (including the DISKUS™ device), WO 97/25086 (including the DISKHALER™ device), WO 95/14089 (including the GEMINI™ device), WO 03/77979 (including the PROHALER™ device), and also the devices disclosed in WO 08/51621, WO 09/117,112 and US 2005/0183724.

The invention also includes (A) the crystalline form of the invention in inhalable form; (B) an inhalable medicament comprising such a crystalline form of the invention in inhalable form together with a pharmaceutically acceptable carrier in inhalable form; (C) a pharmaceutical product comprising such a crystalline form of the invention in inhalable form in association with an inhalation device; and (D) an inhalation device containing such a crystalline form of the invention in inhalable form.

Dosages of agents of the invention employed in practising the present invention will of course vary depending, for example, on the particular condition to be treated, the effect desired and the mode of administration. In general, suitable daily dosages for administration by inhalation are of the order of 0.0001 to 30 mg/kg, typically 0.01 to 10 mg per patient, while for oral administration suitable daily doses are of the order of 0.01 to 100 mg/kg.

The present invention further provides anhydrous pharmaceutical compositions and dosage forms comprising the crystalline form of the invention as active ingredient, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the crystalline form of the invention as an active ingredient will decompose. Such agents, which are referred to herein as "stabilizers," include, but are not limited to, antioxidants such as ascorbic acid, pH buffers, or salt buffers, etc.

The crystalline form of the invention may be administered either simultaneously with, or before or after, one or more other therapeutic agent. The crystalline form of the invention may be administered separately, by the same or different route of administration, or together in the same pharmaceutical composition as the other agents.

In one embodiment, the invention provides a product comprising the crystalline form of the invention and at least one other therapeutic agent as a combined preparation for simultaneous, separate or sequential use in therapy. In one embodiment, the therapy is the treatment of a disease or condition mediated by blockade of the epithelial sodium channel. Products provided as a combined preparation include a composition comprising the crystalline form of the invention and the other therapeutic agent(s) together in the same pharmaceutical composition, or the crystalline form of the invention and the other therapeutic agent(s) in separate form, e.g. in the form of a kit.

In one embodiment, the invention provides a pharmaceutical composition comprising the crystalline form of the invention and another therapeutic agent(s). Optionally, the pharmaceutical composition may comprise a pharmaceutically acceptable excipient, as described above.

In one embodiment, the invention provides a kit comprising two or more separate pharmaceutical compositions, at least one of which contains the crystalline form of the invention.

In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In particular, the crystalline form of the invention exhibits an advantageous stability profile in human plasma. In providing compounds which exhibit an advantageous stability profile in human plasma, the invention provides compounds which effectively blockade the epithelial sodium channel (ENaC) with improved pharmacokinetics.

In the combination therapies of the invention, the crystalline form of the invention and the other therapeutic agent may be manufactured and/or formulated by the same or different manufacturers. Moreover, the crystalline form of the invention and the other therapeutic may be brought together into a combination therapy: (i) prior to release of the combination product to physicians (e.g. in the case of a kit comprising the crystalline form of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a crystalline form of the invention for treating a disease or condition mediated by blockade of the epithelial sodium channel, wherein the medicament is prepared for administration with another therapeutic agent. The invention also provides the use of another therapeutic agent for treating a disease or condition mediated by blockade of the epithelial sodium channel, wherein the medicament is administered with a crystalline form of the invention.

The invention also provides a crystalline form of the invention for use in a method of treating a disease or condition mediated by blockade of the epithelial sodium channel, wherein the crystalline form of the invention is prepared for administration with another therapeutic agent. The invention also provides another therapeutic agent for use in a method of treating a disease or condition mediated by blockade of the epithelial sodium channel, wherein the other therapeutic agent is prepared for administration with the crystalline form of the invention.

The invention also provides the use of the crystalline form of the invention for treating a disease or condition mediated by blockade of the epithelial sodium channel, wherein the patient has previously (e.g. within 24 hours) been treated with another therapeutic agent. The invention also provides the use of another therapeutic agent for treating a disease or condition mediated by blockade of the epithelial sodium channel, wherein the patient has previously (e.g. within 24 hours) been treated with the crystalline form of the invention.

In one embodiment, the other therapeutic agent is selected from anti-inflammatory, bronchodilatory, antihistamine, decongestant and anti-tussive drug substances, particularly in the treatment of cystic fibrosis or obstructive or inflammatory airways diseases such as those mentioned hereinbefore, e.g., as potentiators of therapeutic activity of such drugs or as a means of reducing required dosaging or potential side effects of such drugs.

Accordingly, the invention includes as a further aspect a combination of an epithelial sodium channel blocker of the present invention with osmotic agents (hypertonic saline, dextran, mannitol, Xylitol), modifiers of CFTR function, both wild-type and mutant (correctors and potentiators), e.g., those described in WO2007/021982, WO2006/099256, WO2006/127588, WO2004/080972, WO2005/026137, WO2005/035514, WO2005/075435, WO2004/111014, WO2006/101740, WO2004/110352, WO2005/120497 and US2005/0176761, an anti-inflammatory, bronchodilatory, antihistamine, anti-tussive, antibiotic or DNase drug substance, said epithelial sodium channel blocker and said drug substance being in the same or different pharmaceutical composition.

Suitable modifiers of CFTR function include CFTR potentiators, in particular the compound VX-770 of formula

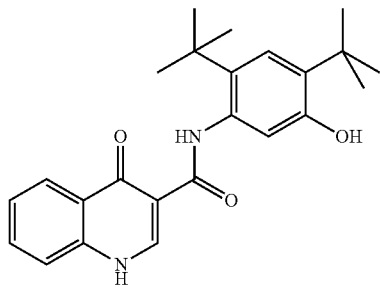 [SMILES: CC(C)(C)c1cc(C(C)(C)C)c(NC(=O)c2c[nH]c3ccccc3c2=O)cc1O]

Suitable antibiotics include macrolide antibiotics, e.g., tobramycin (TOBIT™).

Suitable DNase drug substances include dornase alfa (Pulmozyme™), a highly-purified solution of recombinant human deoxyribonuclease I (rhDNase), which selectively cleaves DNA. Dornase alfa is used to treat cystic fibrosis.

Other useful combinations of epithelial sodium channel blockers with anti-inflammatory drugs are those with antagonists of chemokine receptors, e.g., CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists, such as Schering-Plough antagonists SC-351125, SCH-55700 and SCH-D; Takeda antagonists, such as N-[[4-[[[6,7-dihydro-2-(4-methyl-phenyl)-5H-benzo-cyclohepten-8-yl]carbonyl]amino]phenyl]-methyl] tetrahydro-N,N-dimethyl-2H-pyran-4-amin-ium chloride (TAK-770); and CCR-5 antagonists described in U.S. Pat. No. 6,166,037 (particularly claims 18 and 19), WO00/66558 (particularly claim 8), WO00/66559 (particularly claims 9), WO04/018425 and WO04/026873.

Suitable anti-inflammatory drugs include steroids, in particular, glucocorticosteroids, such as budesonide, beclamethasone dipropionate, fluticasone propionate, ciclesonide or mometasone furoate, or steroids described in WO 02/88167, WO 02/12266, WO 02/100879, WO 02/00679 (especially those of Examples 3, 11, 14, 17, 19, 26, 34, 37, 39, 51, 60, 67, 72, 73, 90, 99 and 101), WO 03/35668, WO 03/48181, WO 03/62259, WO 03/64445, WO 03/72592, WO 04/39827 and WO 04/66920; non-steroidal glucocorticoid receptor agonists, such as those described in DE 10261874, WO 00/00531, WO 02/10143, WO 03/82280, WO 03/82787, WO 03/86294, WO 03/104195, WO 03/101932, WO 04/05229, WO 04/18429, WO 04/19935 and WO 04/26248; LTD4 antagonists, such as montelukast and zafirlukast; PDE4 inhibitors, such as cilomilast (Ariflo® GlaxoSmithKline), Roflumilast (Byk Gulden), V-11294A (Napp), BAY19-8004 (Bayer), SCH-351591 (Schering-Plough), Arofylline (Almirall Prodesfarma), PD189659/PD168787 (Parke-Davis), AWD-12-281 (Asta Medica), CDC-801 (Celgene), SelCID™ CC-10004 (Celgene), VM554/UM565 (Vernalis), T-440 (Tanabe), KW-4490 (Kyowa Hakko Kogyo), and those disclosed in WO 92/19594, WO 93/19749, WO 93/19750, WO 93/19751, WO 98/18796, WO 99/16766, WO 01/13953, WO 03/104204, WO 03/104205, WO 03/39544, WO 04/000814, WO 04/000839, WO 04/005258, WO 04/018450, WO 04/018451, WO 04/018457, WO 04/018465, WO 04/018431, WO 04/018449, WO 04/018450, WO 04/018451, WO 04/018457, WO 04/018465, WO 04/019944, WO 04/019945, WO 04/045607 and WO 04/037805; adenosine A2B receptor antagonists such as those described in WO 02/42298; and beta-2 adrenoceptor agonists, such as albuterol (salbutamol), metaproterenol, terbutaline, salmeterol fenoterol, procaterol, and especially, formoterol, carmoterol and pharmaceutically acceptable salts thereof, and compounds (in free or salt or solvate form) of formula (I) of WO0075114, which document is incorporated herein by reference, preferably compounds of the Examples thereof, especially a compound of formula:

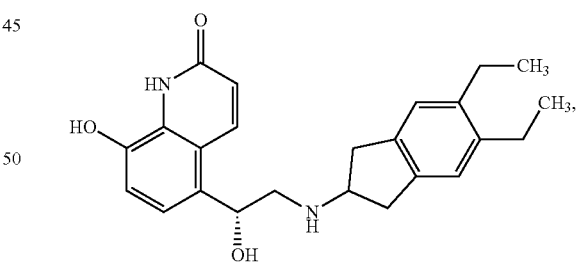

corresponding to indacaterol and pharmaceutically acceptable salts thereof, as well as compounds (in free or salt or solvate form) of formula (I) of WO 04/16601, and also compounds of EP 1440966, JP 05025045, WO 93/18007, WO 99/64035, USP 2002/0055651, WO 01/42193, WO 01/83462, WO 02/66422, WO 02/70490, WO 02/76933, WO 03/24439, WO 03/42160, WO 03/42164, WO 03/72539, WO 03/91204, WO 03/99764, WO 04/16578, WO 04/22547, WO 04/32921, WO 04/33412, WO 04/37768, WO 04/37773, WO 04/37807, WO 04/39762, WO 04/39766, WO 04/45618, WO 04/46083, WO 04/80964, WO 04/108765 and WO 04/108676.

Suitable bronchodilatory drugs include anticholinergic or antimuscarinic agents, in particular, ipratropium bromide, oxitropium bromide, tiotropium salts and CHF 4226 (Chiesi), and glycopyrrolate, but also those described in EP 424021, U.S. Pat. No. 3,714,357, U.S. Pat. No. 5,171,744, WO 01/04118, WO 02/00652, WO 02/51841, WO 02/53564, WO 03/00840, WO 03/33495, WO 03/53966, WO 03/87094, WO 04/018422 and WO 04/05285.

Suitable dual anti-inflammatory and bronchodilatory drugs include dual beta-2 adrenoceptor agonist/muscarinic antagonists such as those disclosed in USP 2004/0167167, WO 04/74246 and WO 04/74812.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine, as well as those disclosed in JP 2004107299, WO 03/099807 and WO 04/026841.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of the crystalline form of the invention refers to an amount of the crystalline form of the invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the crystalline form of the invention that, when administered to a subject, is effective to (1) at least partially alleviating, inhibiting, preventing and/or ameliorating a condition, or a disorder or a disease (i) mediated by the epithelial sodium channel, or (ii) associated with epithelial sodium channel activity, or (iii) characterized by activity (normal or abnormal) of the epithelial sodium channel; or (2) reducing or inhibiting the activity of the epithelial sodium channel. In another non-limiting embodiment, the term "a therapeutically effective amount" refers to the amount of the crystalline form of the invention that, when administered to a cell, or a tissue, or a non-cellular biological material, or a medium, is effective to at least partially reducing or inhibiting the activity of the epithelial sodium channel.

As used herein, the term "subject" refers to an animal. Typically the animal is a mammal. A subject also refers to for example, primates (e.g., humans), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

EXPERIMENTAL

General Conditions:

Mass spectra were run on LCMS systems using electrospray ionization. These were either Agilent 1100 HPLC/Micromass Platform Mass Spectrometer combinations, or Agilent 1200 HPLC/Agilent 6130 Quadropole Mass Spectrometer combinations, or Waters Acquity UPLC with SQD Mass Spectrometer. [M+H]+ refers to mono-isotopic molecular weights.

NMR spectra were run on open access Bruker AVANCE 400 NMR spectrometers using ICON-NMR. Spectra were measured at 298K and were referenced using the solvent peak. Some protons were not observed directly due to the very broad nature of their exchangeable resonances.

If not indicated otherwise, the analytical HPLC conditions are as follows:

Method (i)

| | |
|---|---|
| Column | Agilent Zorbax SB-C18 (Rapid resolution) 30 × 2.1 mm, 3.5 A |
| Column Temperature | 30° C. |
| Eluents | B: $H_2O$, C: acetonitrile, both containing 0.1% formic acid |
| Flow Rate | 0.8 mL/min |
| Gradient | 1 min 5% C; 5% to 95% C in 5 min, 3.00 min 95% C |

Method (ii)

| | |
|---|---|
| Column | SB-C18 50 × 4.6 mm, 1.8 M |
| Column Temperature | 30° C. |
| Eluents | A: $H_2O$, B: acetonitrile, both containing 0.1% formic acid |
| Flow Rate | 1 mL/min |
| Gradient | 1 min 2% B; 2% to 70% B in 4 min, 70% to 90% B in 0.1 min, 4.9 min 95% B |

Method 2minLC__v003

| | |
|---|---|
| Column | Waters BEH C18 50 × 2.1 mm, 1.7 m |
| Column Temperature | 50° C. |
| Eluents | A: $H_2O$, B: acetonitrile, both containing 0.1% TFA |
| Flow Rate | 0.8 mL/min |
| Gradient | 0.20 min 5% B; 5% to 95% B in 1.30 min, 0.25 min 95% B |

ABBREVIATIONS

Br broad
d doublet
DCM dichloromethane
DSC differential scanning calorimetry
DMF N,N-dimethylformamide
DMI 1,3-dimethyl-2-imidazolidinone
DMSO dimethylsulfoxide
EDCI N-(3-dimethylaminopropyl)-N'-ethylcarbodiimide
EtOAc ethyl acetate
h hour(s)
HOBt 1-hydroxybenzotriazole
HPLC high pressure liquid chromatography
LC-MS liquid chromatography and mass spectrometry
MeOH methanol
MS mass spectrometry
m multiplet
2-meTHF 2-methyltetrahydrofuran
min minutes
ml milliliter(s)
m/m mass to mass ratio
m/z mass to charge ratio
NMR nuclear magnetic resonance
iPrOH isopropanol
ppm parts per million
PS polymer supported
PEAX PE-anion exchange (e.g. Isolute® PE-AX columns from Biotage)
Rt retention time
s singlet
SCX-2 strong cation exchange (e.g. Isolute® SCX-2 columns from Biotage)
t triplet
TEA triethylamine
TFA trifluoroacetic acid
THF tetrahydrofuran Preparation 1: 3-(3-{2-[(E)-3,5-Diamino-6-chloro-pyrazine-2-carbonylimino]-1,3,8-triaza-spiro[4.5]decane-8-carbonyl}-benzenesulfonylamino)-propionic acid dipropylcarbamoylmethyl ester

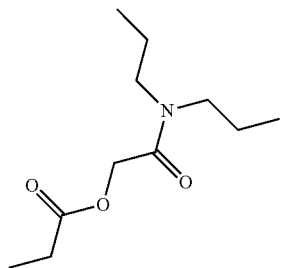
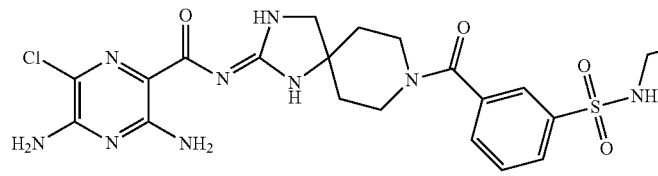

The title compound may be prepared by either Method A or B

Method A:
To a stirred solution of 3-(2-dipropylcarbamoylmethoxy-carbonyl-ethylsulfamoyl)-benzoic acid (may be prepared as in Preparation 2; 6.1 g, 12.60 mmol) in THF (50 ml) was added sequentially water (25 ml), N-methylmorpholine (7 ml, 63 mmol) and HOBt hydrate (2.9 g, 18.9 mmol). The internal temperature was maintained at ≤20° C. 3,5-Diamino-6-chloro-pyrazine-2-carboxylic acid [1,3,8-triaza-spiro[4.5]dec-(2E)-ylidene]-amide hydrochloride (WO09/074,575, Example 38, page 123) (65% purity, 6.3 g, 12.6 mmol) was added and stirred until a clear solution had formed. EDCI.HCl (3.6 g, 18.9 mmol) was added, and the reaction was stirred at RT for 24 h. 2-MeTHF (200 ml) and 2% aq. Na$_2$CO$_3$ (150 ml) were added to the reaction mixture. The layers were separated, and the aqueous phase washed with additional 2-MeTHF (100 ml). The combined organic layers were washed with 2% aq. Na$_2$CO$_3$ (200 ml) and water (2×200 ml). Acetonitrile (100 ml) was added, and the solution concentrated at 30° C. to a volume of 70 ml. Acetonitrile (300 ml) was added, and the solution concentrated again at 30° C. to a volume of 150 ml. The solution was heated to 50° C. and maleic acid (1.62 g) was added to the resulting solution. An off-white precipitate formed immediately, the temperature was allowed to cool to RT over 1 h. The solid was collected by filtration to afford 3-(3-{2-[(E)-3,5-Diamino-6-chloro-pyrazine-2-carbonylimino]-1,3,8-triaza-spiro[4.5]decane-8-carbonyl}-benzenesulfonylamino)-propionic acid dipropylcarbamoylmethyl ester as a maleate salt; DCM (200 ml) and 2% aq. Na$_2$CO$_3$ (200 ml) were added and stirred until the solid had fully dissolved. The organic layer was separated, washed with water (2×100 ml) and concentrated in vacuo to afford the title compound. LC-MS 722.1 [M+H]$^+$, Method (i); $^1$H NMR (400 MHz, DMSO-d6) δ 9.12-7.57 (4H, br), 7.88 (1H, m), 7.77 (1H, m), 7.70 (1H, m), 7.68 (1H, m), 7.05-6.50 (2H, br s), 6.95-6.20 (1H, br s), 4.73 (2H, s), 3.81-3.39 (2H, m), 3.61-3.31 (2H, m), 3.43 (2H, br s), 3.15-3.11 (4H, m), 3.04 (2H, t), 2.51 (2H, t), 1.79-1.69 (m, 4H), 1.51-1.43 (4H, m), 0.84 (3H, t), 0.78 (3H, t)

Method B:
To a stirred solution of 3-(2-dipropylcarbamoylmethoxy-carbonyl-ethylsulfamoyl)-benzoic acid (Int. AA) (6.1 g, 12.60 mmol) in THF (50 ml) was added sequentially water (25 ml), N-methylmorpholine (7 ml, 63 mmol) and HOBt hydrate (2.9 g, 18.9 mmol). The internal temperature was maintained at ≤20° C. 3,5-Diamino-6-chloro-pyrazine-2-carboxylic acid [1,3,8-triaza-spiro[4.5]dec-(2E)-ylidene]-amide hydrochloride (WO09074575, Ex. 38, page 123) (65% purity, 6.3 g, 12.6 mmol) was added and stirred until a clear solution had formed. EDCI.HCl (3.6 g, 18.9 mmol) was added, and the reaction was stirred at RT for 24 h. 2-MeTHF (200 ml) and 2% aq. Na$_2$CO$_3$ (150 ml) were added to the reaction mixture. The layers were separated, and the aqueous phase washed with additional 2-MeTHF (100 ml). The combined organic layers were washed with 2% aq. Na$_2$CO$_3$ (200 ml) and water (2×200 ml). Acetonitrile (100 ml) was added, and the solution concentrated at 30° C. to a volume of 70 ml. Acetonitrile (300 ml) was added, and the solution concentrated again at 30° C. to a volume of 150 ml. The solution was heated to 50° C. and maleic acid (1.62 g) was added to the resulting solution. An off-white precipitate formed immediately, the temperature was allowed to cool to RT over 1 h. The solid was collected by filtration to afford 3-(3-{2-[(E)-3,5-Diamino-6-chloro-pyrazine-2-carbonylimino]-1,3,8-triaza-spiro[4.5]decane-8-carbonyl}-benzenesulfonylamino)-propionic acid dipropylcarbamoylmethyl ester as a maleate salt; DCM (200 ml) and 2% aq. Na$_2$CO$_3$ (200 ml) were added and stirred until the solid had fully dissolved. The organic layer was separated, washed with water (2×100 ml) and concentrated in vacuo to afford the title compound. LC-MS 722.1 [M+H]$^+$, Method (i); $^1$H NMR (400 MHz, DMSO-d6) δ 9.12-7.57 (4H, br), 7.88 (1H, m), 7.77 (1H, m), 7.70 (1H, m), 7.68 (1H, m), 7.05-6.50 (2H, br s), 6.95-6.20 (1H, br s), 4.73 (2H, s), 3.81-3.39 (2H, m), 3.61-3.31 (2H, m), 3.43 (2H, br s), 3.15-3.11 (4H, m), 3.04 (2H, t), 2.51 (2H, t), 1.79-1.69 (m, 4H), 1.51-1.43 (4H, m), 0.84 (3H, t), 0.78 (3H, t)

Preparation 2: 3-(2-Dipropylcarbamoylmethoxycarbonyl-ethylsulfamoyl)-benzoic acid

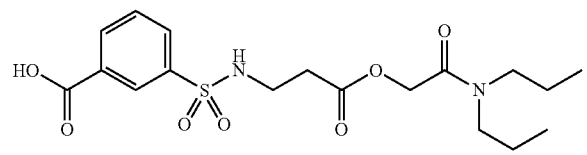 [SMILES: CCCN(CCC)C(=O)COC(=O)CCNS(=O)(=O)c1cccc(C(=O)O)c1]

The title compound may be prepared by either Method A or B:

Method A:

Step 1: 3-Benzyloxycarbonylamino-propionic acid dipropylcarbamoylmethyl ester

To a solution of benzyloxycarbonylamino-propionic acid (22.3 g, 99.9 mmol) in DMF (150 ml) was added potassium carbonate (19.3 g, 139.9 mmol). 2-Chloro-N,N-dipropyl-acetamide (17.7 g, 99.9 mmol) was added over 30 min, and the reaction mixture was heated to 60° C. and stirred for 2.5 h. The reaction mixture was allowed to cool to RT and diluted with water (500 ml) and extracted with isopropyl acetate (total 500 ml). The combined organic phases were washed with water (3×200 ml) to afford a solution of 3-benzyloxycarbonylamino-propionic acid dipropylcarbamoylmethyl ester in isopropyl acetate which was not isolated further. LC-MS; 365.2 [M+H]$^+$ Method (i)

Step 2: 3-Amino-propionic acid dipropylcarbamoylmethyl ester trifluoroacetate

A solution of 3-benzyloxycarbonylamino-propionic acid dipropylcarbamoylmethyl ester in isopropyl acetate (33.2 g, 91.0 mmol in 129.9 g total mass of solution) was treated with TFA (7.05 ml, 92.0 mmol) while the internal temperature was maintained at 20° C., followed by 10% Pd/C (3.3 g, 50% wet) and stirred under an atmosphere of H$_2$ (3 atm) for 3.5 h to afford 3-amino-propionic acid dipropylcarbamoylmethyl ester trifluoroacetate. The solution was used directly in the next reaction without isolation.

Step 3: Benzyl 3-(2-Dipropylcarbamoylmethoxycarbonyl-ethylsulfamoyl)-benzoic acid benzyl ester A solution of 3-amino-propionic acid dipropylcarbamoylmethyl ester trifluoroacetate (25.4 g 73.8 mmol) in isopropyl acetate was cooled to 0° C. and treated with N-methylmorpholine (26.3 g, 221.5 mmol), water (40 ml) and DMAP (90.4 mg, 0.74 mmol). 3-Chlorosulfonyl-benzoic acid benzyl ester (24.1 g, 77.5 mmol) in isopropyl acetate (44 ml) was added and the reaction mixture was stirred for 2 h at 0-5° C. The layers were separated and the organic phase was washed with sat. aq. NaHCO$_3$ (3×26 ml), diluted with water (10 ml), the pH adjusted to 6 with 1N HCl solution, and washed with brine. The resulting solution was concentrated to provide a solution of benzyl 3-(2-Dipropylcarbamoylmethoxycarbonyl-ethylsulfamoyl)-benzoic acid benzyl ester in isopropyl acetate which was used in further reactions without isolation. LC-MS; [M+H]$^+$ 505.1 Method (i)

Step 4: Synthesis of 3-(2-Dipropylcarbamoylmethoxycarbonyl-ethylsulfamoyl)-benzoic acid A solution of benzyl 3-(2-Dipropylcarbamoylmethoxycarbonyl-ethylsulfamoyl)-benzoic acid benzyl ester (5 g, 33.25 mmol) in isopropyl acetate (82 ml) was treated with 10% Pd/C (0.84 g, 50% wet), and stirred under H$_2$ (3 atm) overnight. The catalyst was removed by filtration. To the filtrate was added 10% Pd/C (1.68 g, 50% wet), and the reaction stirred under H$_2$ (3 atm) for 18 h. The catalyst was removed by filtration and further 10% Pd/C (1.68 g, 50% wet) was added and the reaction stirred under H$_2$ (1 atm) for 18 h. The catalyst was removed by filtration and washed with isopropyl acetate (20 ml). The combined filtrates were concentrated in vacuo and heptane was added to the solution and stirred at RT for 2 hr then −2° C. for 4 h. The solid which formed was collected by filtration and dried under vacuum at 40° C. to afford the title compound; LC-MS; 415.1 [M+H]$^+$, Method (i).

Method B:

Step 1: 3-tert-Butoxycarbonylamino-propionic acid dipropylcarbamoylmethyl ester

To a stirred suspension of Boc-Beta-Ala-OH (40.0 g, 211 mmol) in DMF (200 ml) at 60° C. under N$_2$ was added potassium carbonate (40.0 g, 289 mmol). To this mixture was added 2-chloro-N,N-dipropyl-acetamide (36.7 g, 207 mmol) in DMF (75 ml). The reaction mixture was allowed to stir at 60° C. overnight. The reaction was allowed to cool to RT and diluted with DCM (400 ml) followed by water (500 ml). The organic layer was separated and washed with brine (200 ml), dried over MgSO$_4$ and concentrated in vacuo to yield a pale yellow oil. To the oil was added n-heptane (500 ml) (azeotrope for DMF) which was concentrated in vacuo to afford the title compound; LC-MS Rt 1.14 mins; 331.3 [M+H]$^+$, Method 2minLC_v003.

Step 2: 3-Amino-propionic acid dipropylcarbamoylmethyl ester

To a cooled stirred solution of 3-tert-butoxycarbonylamino-propionic acid dipropylcarbamoylmethyl ester (step 1) (36.5 g, 110 mmol) in dry dioxane under N$_2$ was added dropwise 4N HCl in dioxane (18.12 ml, 597 mmol). The resulting mixture was allowed to warm to RT and stirred overnight. The solvent was removed in vacuo and the crude product was suspended in EtOAc (500 ml) and sonicated for 1 h. The resulting white precipitate was isolated by filtration and was dried under vacuum at 40° C. for 1 h to afford a pale yellow solid. Recrystallisation from EtOAc afforded the title compound; LC-MS Rt 0.77 mins; 231.2 [M+H]$^+$, Method 2minLC_v003.

Step 3: 3-(2-Dipropylcarbamoylmethoxycarbonyl-ethylsulfamoyl)-benzoic acid

To a stirred solution of 3-amino-propionic acid dipropylcarbamoylmethyl ester (step 2) (20.1 g, 75 mmol) in DCM (240 ml) at 0° C. under $N_2$ was added DMAP (0.46 g, 3.76 mmol) followed by TEA (38.8 ml, 278 mmol). The reaction mixture was treated with a solution of 3-chlorosulfonylbenzoic acid (16.6 g, 75 mmol) in DCM (200 ml). The mixture was allowed to stir at 0° C. for 1 h and then warmed up to RT for 1 h. Water (200 ml) was added and the pH adjusted with 1N HCl (100 ml). The organic layer was separated, dried over $MgSO_4$ and concentrated in vacuo. Purification by C18 reverse phase chromatography, eluting with MeCN/water (1% HCl) afforded the title product; LC-MS Rt 1.01 mins; 415.2 [M+H]$^+$, Method 2minLC_v003.

Example 1

3-(3-{2-[(E)-3,5-Diamino-6-chloro-pyrazine-2-carbonylimino]-1,3,8-triaza-spiro[4.5]decane-8-carbonyl}-benzenesulfonylamino)-propionic acid dipropylcarbamoylmethyl ester succinate salt: Preparation of crystalline form A 2.5 g of 3-(3-{2-[(E)-3,5-Diamino-6-chloro-pyrazine-2-carbonylimino]-1,3,8-triaza-spiro[4.5]decane-8-carbonyl}-benzenesulfonylamino)-propionic acid dipropylcarbamoylmethyl ester (may be prepared as in Preparation 1; 3.47 mmol) were dissolved in 25 mL acetonitrile and 1.5 mL water at 50° C. 409 mg succinic acid (3.47 mmol) was added. The acid dissolved immediately and the clear solution was cooled down to room temperature over 30 minutes. At approximately 30° C. the crystallization took place. The slurry was then stirred for approximately 16 h at room temperature. The crystals were collected by filtration. The filter cake was washed in portions with 9 ml acetonitrile/water 95:5 v/v and dried for 16 h at 50° C. and at around 10 mbar.

Example 2

3-(3-{2-[(E)-3,5-Diamino-6-chloro-pyrazine-2-carbonylimino]-1,3,8-triaza-spiro[4.5]decane-8-carbonyl}-benzenesulfonylamino)-propionic acid dipropylcarbamoylmethyl ester succinate salt: Preparation of crystalline form A A mixture comprising succinic acid (0.50 g, 4.23 mmol) and acetone (20 g) was heated to 45° C. until a clear solution formed and then filtered (0.2 μm PTFE filter).
In a second reaction vessel, 3-(3-{2-[(E)-3,5-diamino-6-chloro-pyrazine-2-carbonylimino]-1,3,8-triaza-spiro[4.5] decane-8-carbonyl}-benzenesulfonylamino)-propionic acid dipropylcarbamoylmethyl ester (Preparation 1, Method B)(3.00 g, 4.16 mmol) and acetone (30 g) were heated to 45° C. until a clear solution formed and then filtered (0.2 μm PTFE filter).
The solution of succinic acid (0.50 g, 4.23 mmol) in acetone (20 ml) was heated at 45° C. for 1 h and treated with a portion of the solution of 3-(3-{2-[(E)-3,5-diamino-6-chloro-pyrazine-2-carbonylimino]-1,3,8-triaza-spiro[4.5] decane-8-carbonyl}-benzenesulfonyl amino)-propionic acid dipropylcarbamoylmethyl ester in acetone (1.62 g of solution) over 10 min. The resulting mixture was treated with a suspension of seed crystals of 3-(3-{2-[(E)-3,5-diamino-6-chloro-pyrazine-2-carbonylimino]-1,3,8-triaza-spiro[4.5] decane-8-carbonyl}-benzenesulfonylamino)-propionic acid dipropylcarbamoylmethyl ester succinate salt (as prepared using the preparation of Example 1, 20 mg) in acetone (300 mg) and stirred at 45° C. for 30 min. The remaining solution of 3-(3-{2-[(E)-3,5-diamino-6-chloro-pyrazine-2-carbonylimino]-1,3,8-triaza-spiro[4.5]decane-8-carbonyl}-benzenesulfonyl amino)-propionic acid dipropylcarbamoyl methyl ester in acetone (31.38 g) was added to the mixture over 5 h and heating continued at 45° C. for 1 h. The suspension was cooled to 25° C. over 1 h and stirred for a further 1 h. The suspension was filtered over a glass frit and the filter cake was washed with acetone (2×5 g). The filter cake was dried at 50° C. to afford the title compound; HPLC Rt 4.02 min, method ii; $^1$H NMR (400 MHz, DMSO-d6) δ 7.87 (1H, m), 7.78 (1H, m), 7.69 (1H, m), 7.68 (1H, m), 6.85 (2H, br s), 4.73 (2H, s), 3.84-3.20 (6H and water, br hump), 3.17-3.09 (4H, m), 3.04 (2H, t), 2.53 (2H, under DMSO), 2.39 (4H, s), 1.80 (2H, br s), 1.70 (2H, br s), 1.55-1.37 (4H, m), 0.85 (3H, t), 0.78 (3H, t) (Please note: The two exchangeable succinate protons and 3-4 acidic NH resonances were not observed directly due to the very broad nature of some of the exchangeable resonances; Melting Temperature $T_m$ (DSC)=149° C.

Example 3

3-(3-{2-[(E)-3,5-Diamino-6-chloro-pyrazine-2-carbonylimino]-1,3,8-triaza-spiro[4.5]decane-8-carbonyl}-benzenesulfonylamino)-propionic acid dipropylcarbamoylmethyl ester succinate salt: Preparation of crystalline form A 3 g of 3-(3-{2-[(E)-3,5-Diamino-6-chloro-pyrazine-2-carbonylimino]-1,3,8-triaza-spiro[4.5]decane-8-carbonyl}-benzenesulfonylamino)-propionic acid dipropylcarbamoylmethyl ester succinate salt (may be prepared as shown in Example 1 or 2) was charged into an 100 ml reactor equipped with an anchor stirrer (150 rpm), condenser, dosing unit and turbidity probe. 20 g of an acetone/water mixture (92.5/7.5 m/m) was added and the whole heated to 50 C and stirred until all was dissolved. The reaction mixture was then cooled to 45 C. 30 mg of seed crystals (may be prepared as shown in Example 1 or 2) suspended in 300 mg acetone was added. The reaction mixture was then cooled to 25 C over 1 hour. The whole was stirred for 3.5 hours. 28 ml EtOAc was then added over 2 hours. The reaction mixture was further cooled to 0 C over 1 hour and the whole then stirred overnight. The reaction mixture was filtered through a glass frit and the obtained solid was then washed twice with 5 ml acetone and dried at 40 C at 1 mbar for 24 hours.

Example 4

3-(3-{2-[(E)-3,5-Diamino-6-chloro-pyrazine-2-carbonylimino]-1,3,8-triaza-spiro[4.5]decane-8-carbonyl}-benzenesulfonylamino)-propionic acid dipropylcarbamoylmethyl ester succinate salt: Preparation of crystalline form B 3 g of 3-(3-{2-[(E)-3,5-Diamino-6-chloro-pyrazine-2-carbonylimino]-1,3,8-triaza-spiro[4.5]decane-8-carbonyl}-benzenesulfonylamino)-propionic acid dipropylcarbamoylmethyl ester (may be prepared as in Preparation 1) was dissolved in 22.7 g of acetone at 50° C. in a 100 mL glass reactor equipped with an anchor stirrer (150 rpm). 5 mL of succinic acid solution (2.94 weight % in acetone) was added to the reactor. 10 mg of 3-(3-{2-[(E)-3,5-Diamino-6-chloro-pyrazine-2-carbonylimino]-1,3,8-triaza-spiro[4.5]decane-8-carbonyl}-benzenesulfonylamino)-propionic acid dipropylcarbamoylmethyl ester succinate salt, crystalline form A (may be prepared as in Example 1 or 2), was suspended in 0.2 g acetone, sonicated, and added to the reactor. Another 40 mL of succinic acid solution (2.94 weight % in acetone) were slowly added to the reactor over 20 h. Afterwards, the mixture was cooled to 20° C. and then further stirred for 19 h. The resulting suspension is filtered and the filter cake is washed with 10 g acetone at room temperature twice.

Example 5

3-(3-{2-[(E)-3,5-Diamino-6-chloro-pyrazine-2-carbonylimino]-1,3,8-triaza-spiro[4.5]decane-8-carbonyl}-benzenesulfonylamino)-propionic acid dipropylcarbamoylmethyl ester succinate salt: Preparation of crystalline form B 3 g of 3-(3-{2-[(E)-3,5-Diamino-6-chloro-pyrazine-2-carbonylimino]-1,3,8-triaza-spiro[4.5]decane-8-carbonyl}-benzenesulfonylamino)-propionic acid dipropylcarbamoylmethyl ester (may be prepared as in Preparation 1) and 0.5 g succinic acid were dissolved in a mixture of 28.5 g acetone and 1.5 g water at 50° C. in a 100 mL glass reactor equipped with an anchor stirrer (150 rpm). Afterwards, the solution was cooled to 20° C. 7 mg of 3-(3-{2-[(E)-3,5-Diamino-6-chloro-pyrazine-2-carbonylimino]-1,3,8-triaza-spiro[4.5]decane-8-carbonyl}-benzenesulfonylamino)-propionic acid dipropylcarbamoylmethyl ester succinate salt, crystalline form A (may be prepared as in Example 1 or 2), is suspended in 0.18 g acetone/water 95:5 (v/v), sonicated, and added to the reactor. The mixture was stirred at 20° C. for 15 hours followed by cooling to 0° C. in 10 min. The resulting suspension was filtered and the filter cake washed with 10 g acetone/water 95/5 (v/v) at room temperature.

Example 6

3-(3-{2-[(E)-3,5-Diamino-6-chloro-pyrazine-2-carbonylimino]-1,3,8-triaza-spiro[4.5]decane-8-carbonyl}-benzenesulfonylamino)-propionic acid dipropylcarbamoylmethyl ester succinate salt: Preparation of crystalline form B 0.536 g of 3-(3-{2-[(E)-3,5-Diamino-6-chloro-pyrazine-2-carbonylimino]-1,3,8-triaza-spiro[4.5]decane-8-carbonyl}-benzenesulfonylamino)-propionic acid dipropylcarbamoylmethyl ester (may be prepared as in Preparation 1) and 0.12 g succinic acid were dissolved in 15.25 g 2-propanol at 50° C. in a magnetically stirred glass vial. The solution was cooled to 20° C. and then stirred at this temperature overnight. The resulting suspension was filtered.

Example 7

3-(3-{2-[(E)-3,5-Diamino-6-chloro-pyrazine-2-carbonylimino]-1,3,8-triaza-spiro[4.5]decane-8-carbonyl}-benzenesulfonylamino)-propionic acid dipropylcarbamoylmethyl ester succinate salt: Preparation of crystalline form B 0.535 g of 3-(3-{2-[(E)-3,5-Diamino-6-chloro-pyrazine-2-carbonylimino]-1,3,8-triaza-spiro[4.5]decane-8-carbonyl}-benzenesulfonylamino)-propionic acid dipropylcarbamoylmethyl ester (may be prepared as in Preparation 1) and 0.12 g succinic acid were dissolved in 7.27 g methyl ethyl ketone at 60° C. in a magnetically stirred glass vial. The solution was cooled to 20° C. and then stirred at this temperature overnight. The resulting suspension was filtered.

Example 8

3-(3-{2-[(E)-3,5-Diamino-6-chloro-pyrazine-2-carbonylimino]-1,3,8-triaza-spiro[4.5]decane-8-carbonyl}-benzenesulfonylamino)-propionic acid dipropylcarbamoylmethyl ester succinate salt: Preparation of crystalline form C 3 g of 3-(3-{2-[(E)-3,5-Diamino-6-chloro-pyrazine-2-carbonylimino]-1,3,8-triaza-spiro[4.5]decane-8-carbonyl}-benzenesulfonylamino)-propionic acid dipropylcarbamoylmethyl ester (may be prepared as in Preparation 1) was dissolved in 80.3 g ethanol at 60° C. in a 100 mL glass reactor equipped with anchor stirrer (150 rpm). 25 mL of a succinic acid solution (2.94 weight % in ethanol) was added to the solution followed by the addition of 2.5 g water. The resulting mixture was cooled to 30° C. 5 mg of seed crystals of 3-(3-{2-[(E)-3,5-diamino-6-chloro-pyrazine-2-carbonylimino]-1,3,8-triaza-spiro[4.5]decane-8-carbonyl}-benzenesulfonylamino)-propionic acid dipropylcarbamoylmethyl ester succinate salt, form A (may be prepared using the preparation of Example 1 or 2) was suspended in 0.1 g ethanol, sonicated, and added to the reactor. The resulting mixture was stirred for 96 h (150 rpm). Afterwards, crystals were collected by filtration. The filter cake was dried at 40° C. and 30 mbar for 24 hours.

Example 9

3-(3-{2-[(E)-3,5-Diamino-6-chloro-pyrazine-2-carbonylimino]-1,3,8-triaza-spiro[4.5]decane-8-carbonyl}-benzenesulfonylamino)-propionic acid dipropylcarbamoylmethyl ester succinate salt: Preparation of crystalline form C 1 g of 3-(3-{2-[(E)-3,5-Diamino-6-chloro-pyrazine-2-carbonylimino]-1,3,8-triaza-spiro[4.5]decane-8-carbonyl}-benzenesulfonylamino)-propionic acid dipropylcarbamoylmethyl ester (may be prepared as in Preparation 1) and 0.18 g succinic acid were dissolved in 7.97 g methanol in a glass vial at 50° C. The solution was cooled to 0° C. and then stirred at that temperature for 24 hours. Afterwards, crystals were collected by filtration and dried at 60° C. and 1 mbar for 3 hours. Off-white to yellowish crystals of form C were obtained.

Example 10

3-(3-{2-[(E)-3,5-Diamino-6-chloro-pyrazine-2-carbonylimino]-1,3,8-triaza-spiro[4.5]decane-8-carbonyl}-benzenesulfonylamino)-propionic acid dipropylcarbamoylmethyl ester succinate salt: Preparation of crystalline form C 10.1 Preparation of Seed Crystals:
In an 100 ml reactor equipped with an anchor stirrer (150 rpm), condenser, dosing unit and turbidity probe, 6 g of 3-(3-{2-[(E)-3,5-Diamino-6-chloro-pyrazine-2-carbonylimino]-1,3,8-triaza-spiro[4.5]decane-8-carbonyl}-benzenesulfonylamino)-propionic acid dipropylcarbamoylmethyl ester succinate salt (may be prepared as shown in Example 1 or 2)

were suspended in 27 g of an acetone/water mixture (92.5/7.5 m/m). The suspension was heated to 50 C until the material was dissolved. 40 mg of 3-(3-{2-[(E)-3,5-Diamino-6-chloro-pyrazine-2-carbonylimino]-1,3,8-triaza-spiro[4.5]decane-8-carbonyl}-benzenesulfonylamino)-propionic acid dipropyl-carbamoylmethyl ester succinate salt (prepared as shown in Example 9) in 600 mg acetone, which had been sonicated for 5 minutes, was added and the whole stirred for 6 hours. 76 ml of EtOAc was added over 4 hours and the reaction mixture was then cooled to 25 C over 2 hours. The precipitate was filtered and washed twice with 10 ml acetone and then dried at 60 C under 10 mbar overnight. The resulting solid was then micronized using a spiral jet mill at 5 bar.

10.2 Preparation of Crystalline Form C:

3 g of 3-(3-{2-[(E)-3,5-Diamino-6-chloro-pyrazine-2-carbonylimino]-1,3,8-triaza-spiro[4.5]decane-8-carbonyl}-benzenesulfonylamino)-propionic acid dipropylcarbamoylmethyl ester succinate salt (may be prepared as shown in Example 1 or 2) was charged into an 100 ml reactor equipped with an anchor stirrer (150 rpm), condenser, dosing unit and turbidity probe. 29.5 g of an acetone/water mixture (92.5/7.5 m/m) was added and the whole heated to 50 C and stirred until all was dissolved. 90 mg of seed crystals (see 10.1) suspended in 300 mg acetone was added and the whole stirred for 4 hours. 38 ml EtOAc was added over 4 hours and the reaction mixture was then stirred for 2 hours followed by cooling to 25 C over 2 hours. The whole was stirred overnight and then filtered through a glass frit. The obtained solid was then washed twice with 5 ml acetone and dried at 40 C at 10 mbar for 24 hours.

Characterization of crystalline forms of 3-(3-{2-[(E)-3,5-Diamino-6-chloro-pyrazine-2-carbonylimino]-1,3,8-triaza-spiro[4.5]decane-8-carbonyl}-benzenesulfonylamino)-propionic acid dipropylcarbamoylmethyl ester succinate salt:

All X-ray powder diffraction patterns were recorded in reflection mode.

Figure 1:
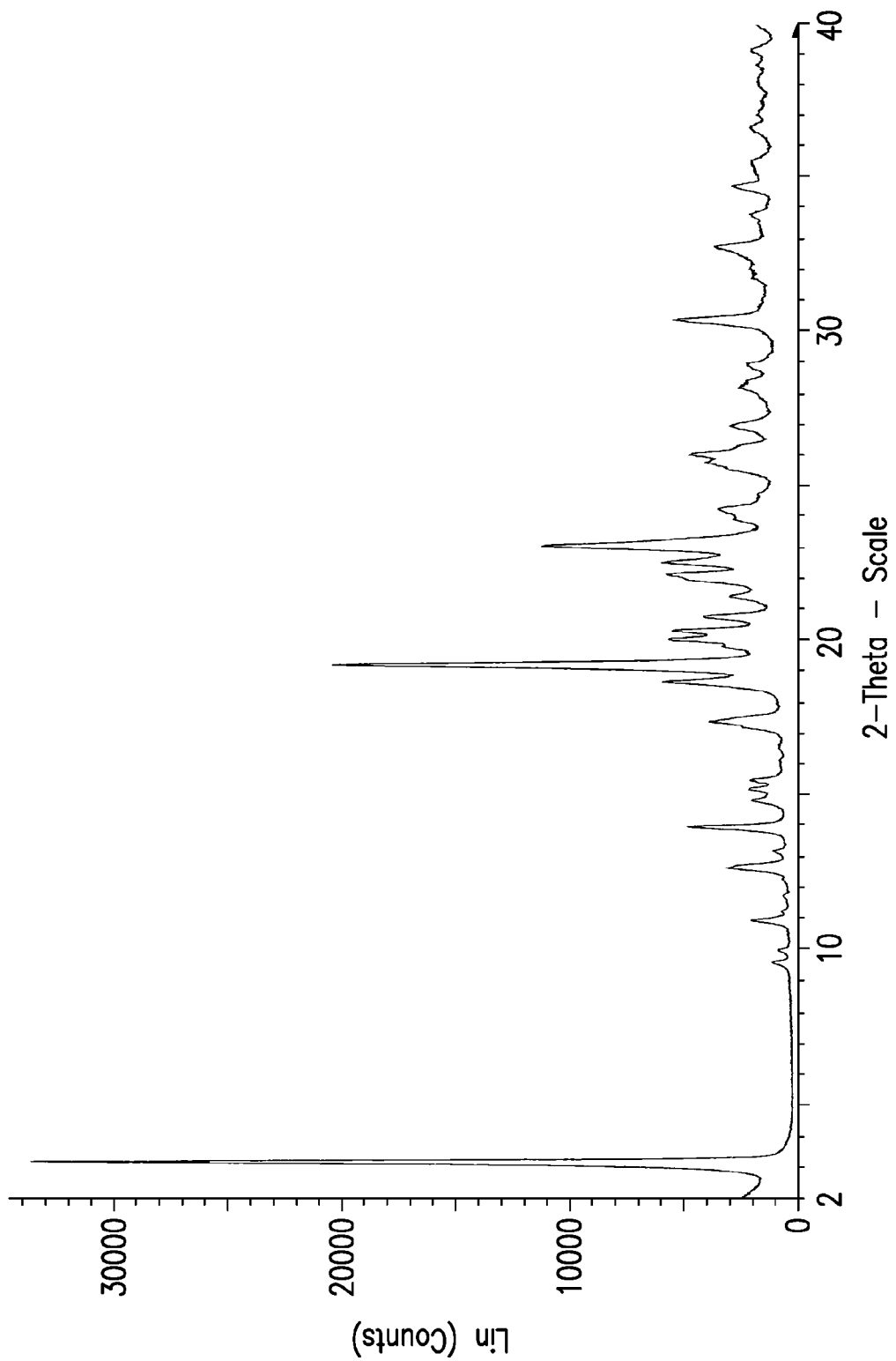
FIG. 1 shows the x-ray powder diffraction pattern recorded for Form A (Example 3) and was recorded on a Bruker™ D8 diffractometer using CuKα radiation (λ=1.5418 Å).

Form A:

a) X-ray powder diffraction a1) An x-ray powder diffraction pattern was recorded on a Bruker™ D8 diffractometer using CuKα radiation (λ=1.5418 Å). The X-ray diffraction pattern of Example 3 thus determined is shown in FIG. 1 and represented in Table 1 below by the reflection lines of the most important lines. The error limit for the 2-Theta angles is ±0.2°.

TABLE 1

Figure 4:
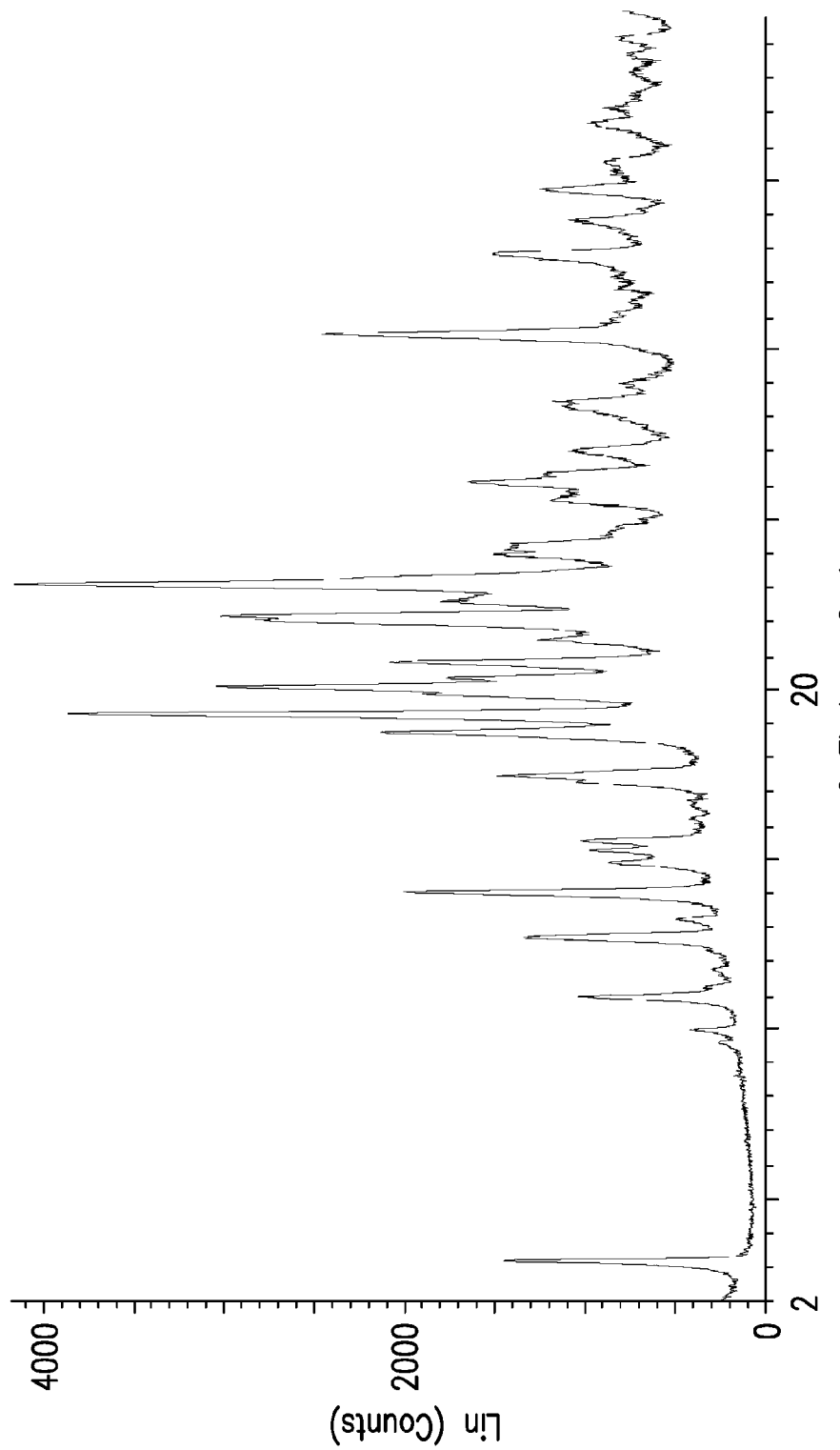
FIG. 4 shows the x-ray powder diffraction pattern recorded for Form A (Example 1, 2) and was recorded on a Bruker™ D8 diffractometer using CuKα radiation (λ=1.5418 Å).

| Angle 2-Theta ° | d value Angstrom | Intensity % |
|---|---|---|
| 3.2 | 27.79210 | 100 |
| 11.0 | 8.06447 | 6 |
| 12.7 | 6.94945 | 9 |
| 14.0 | 6.30426 | 14 |
| 14.9 | 5.94212 | 6 |
| 15.3 | 5.79615 | 6 |
| 15.6 | 5.69030 | 6 |
| 17.5 | 5.07298 | 11 |
| 18.8 | 4.72745 | 18 |
| 19.3 | 4.59524 | 61 |
| 19.8 | 4.47594 | 9 |
| 20.1 | 4.41469 | 17 |
| 20.4 | 4.35953 | 16 |
| 20.8 | 4.26419 | 12 |
| 21.5 | 4.13266 | 9 |
| 22.2 | 4.00651 | 17 |
| 22.6 | 3.93512 | 18 |
| 23.1 | 3.84491 | 33 |
| 24.0 | 3.70349 | 8 |
| 24.3 | 3.66068 | 10 |
| 24.7 | 3.59591 | 5 |
| 25.6 | 3.47462 | 9 |
| 25.9 | 3.44221 | 12 |
| 26.1 | 3.41016 | 14 |
| 26.4 | 3.37500 | 8 |
| 27.0 | 3.29534 | 9 |
| 28.3 | 3.15131 | 7 |
| 29.0 | 3.07534 | 6 |
| 30.5 | 2.93136 | 16 |
| 32.8 | 2.72599 | 11 |
| 33.8 | 2.64794 | 6 |
| 34.7 | 2.58032 | 8 |
| 35.6 | 2.52249 | 6 |
| 36.7 | 2.44894 | 6 |
| 38.7 | 2.32439 | 5 |
| 39.2 | 2.29807 | 6 | a2) An x-ray powder diffraction pattern was recorded on a Bruker™ D8 diffractometer using CuKα radiation (λ=1.5418 Å). The X-ray diffraction pattern thus determined for Example 1 or 2 is shown in FIG. 4 and represented in Table 2 below by the reflection lines of the most important lines. The error limit for the 2-Theta angles is ±0.2°.

TABLE 2

| Angle [2-Theta°] | d value [Angstrom] |
|---|---|
| 3.2 | 27.82660 |
| 10.9 | 8.08104 |
| 12.7 | 6.96126 |
| 14.0 | 6.31327 |
| 14.9 | 5.94185 |
| 15.3 | 5.80195 |
| 15.5 | 5.69596 |
| 17.2 | 5.13947 |
| 17.5 | 5.07677 |
| 18.7 | 4.73387 |
| 19.3 | 4.60047 |
| 19.8 | 4.47276 |
| 20.1 | 4.41948 |
| 20.3 | 4.36135 |
| 20.8 | 4.26679 |
| 21.5 | 4.13483 |
| 22.2 | 4.00989 |
| 22.6 | 3.93071 |
| 23.1 | 3.84729 |
| 24.0 | 3.70743 |
| 24.2 | 3.67477 |
| 24.7 | 3.59652 |
| 25.6 | 3.47835 |
| 26.1 | 3.41096 |
| 26.4 | 3.37922 |
| 27.0 | 3.29646 |
| 27.7 | 3.21774 |
| 28.5 | 3.13361 |
| 29.0 | 3.07785 |
| 30.5 | 2.93279 |
| 31.8 | 2.80895 |
| 32.8 | 2.72626 |
| 33.8 | 2.64887 |
| 34.7 | 2.58155 |
| 35.5 | 2.52537 |
| 36.3 | 2.47491 |
| 36.7 | 2.44931 |
| 37.1 | 2.41984 |
| 37.5 | 2.39660 |
| 38.2 | 2.35582 |
| 38.7 | 2.32643 |
| 39.2 | 2.29792 | b) Elemental analysis:
Water content (Karl Fischer titration): <0.2% m/m

TABLE 3

| Element | theoretical content [% m/m] | measured content [% m/m] |
|---|---|---|
| C | 48.65 | 48.19 |
| H | 5.64 | 5.18 |
| N | 16.69 | 16.66 |
| S | 3.82 | 3.62 |
| O | 20.97 | 21.04 |
| Cl | 4.22 | 4.18 |

Experimental data correspond to expectations for a 1:1 salt formed by 3-(3-{2-[(E)-3,5-diamino-6-chloro-pyrazine-2-carbonylimino]-1,3,8-triaza-spiro[4.5]decane-8-carbonyl}-benzenesulfonylamino)-propionic acid dipropylcarbamoyl-methyl ester and succinic acid.

c) Differential scanning calorimetry (DSC):

DSC traces were recorded on a Perkin Elmer Diamond DSC instrument with aluminium pan (Perkin Elmer, type BO14-3018); heating rate 20 K/min, temperature range: 30 to 250° C.

Figure 2:
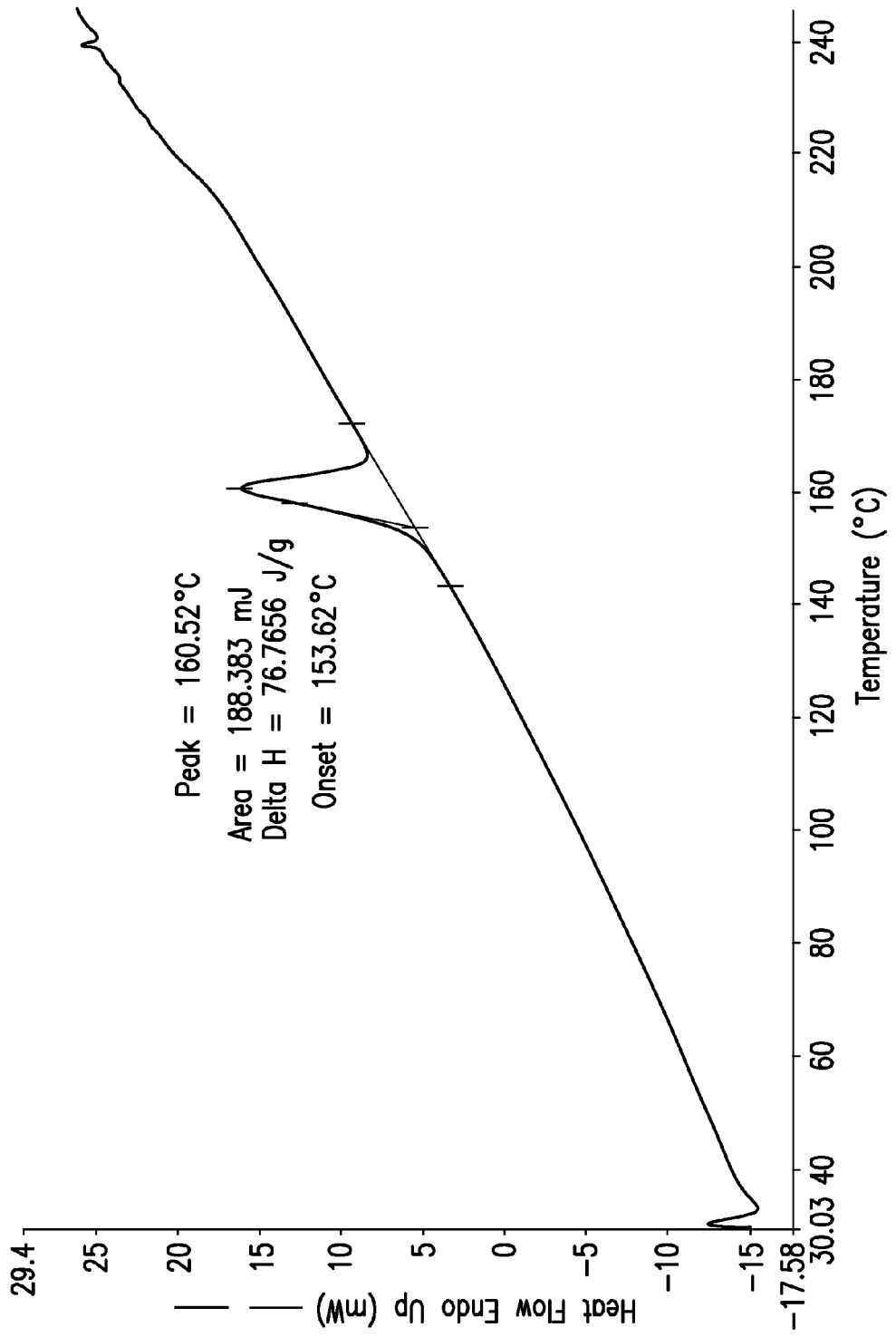
FIG. 2 shows the differential scanning calorimetry (DSC) trace of Form A (Example 3) and was recorded on a Perkin Elmer Diamond DSC instrument with aluminium pan (Perkin Elmer, type BO14-3018); heating rate 20 K/min, temperature range: 30 to 250° C.

FIG. 2 shows the DSC trace of Form A. Melting endotherm: $T_{onset}$=153.6° C., ΔH=76.8 J/g.

Figure 3:
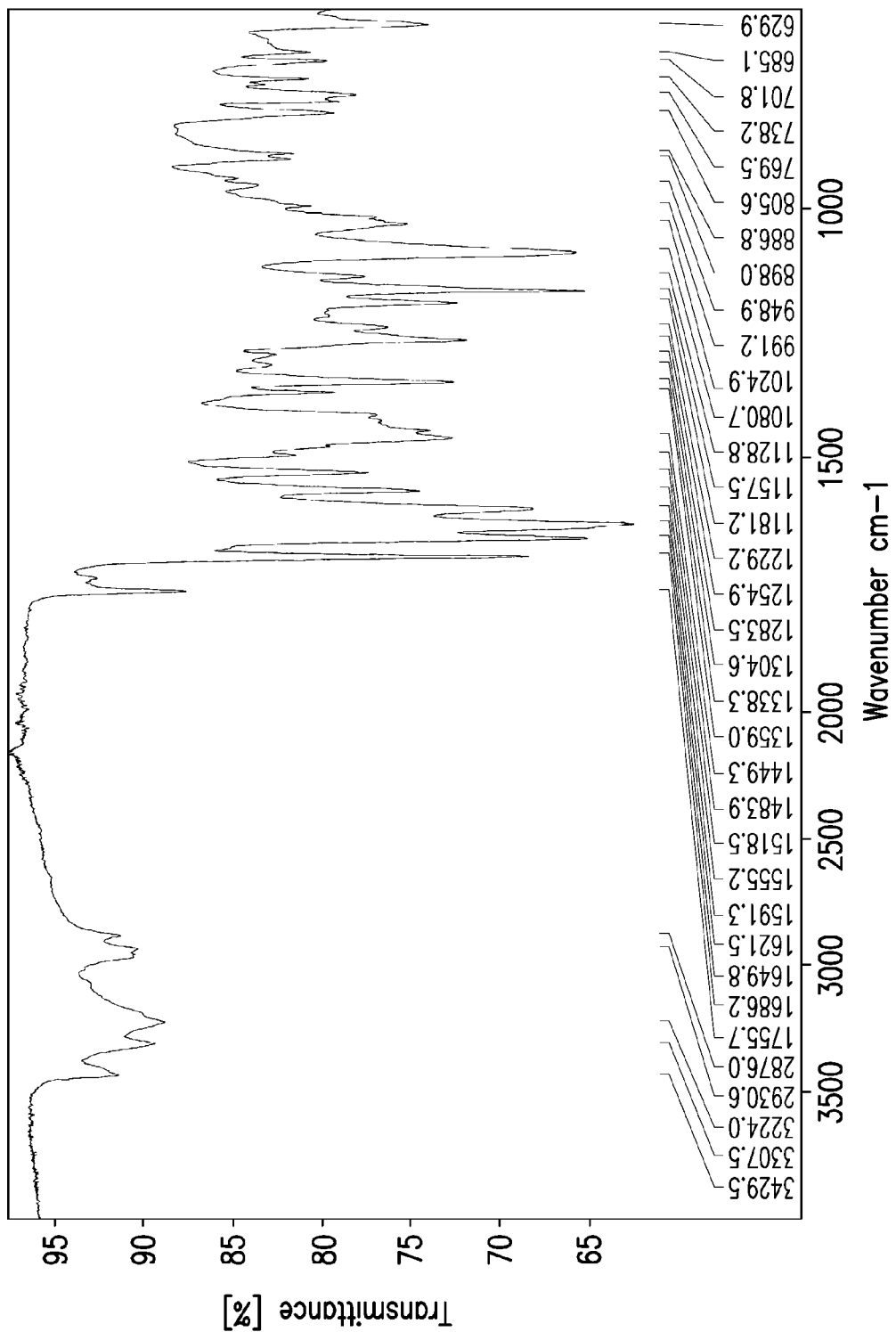
FIG. 3 shows an infrared spectrum of Form A (Example 3) and was recorded on a Bruker Alpha instrument in attenuated total reflection (ATR) mode. Measurement parameters were as follows: range 400-4000 cm$^{-1}$, resolution 2 cm$^{-1}$, 64 scans, velocity 7.5 kHz, apodisation: Blackman-Harris 3-term.
Figure 5:
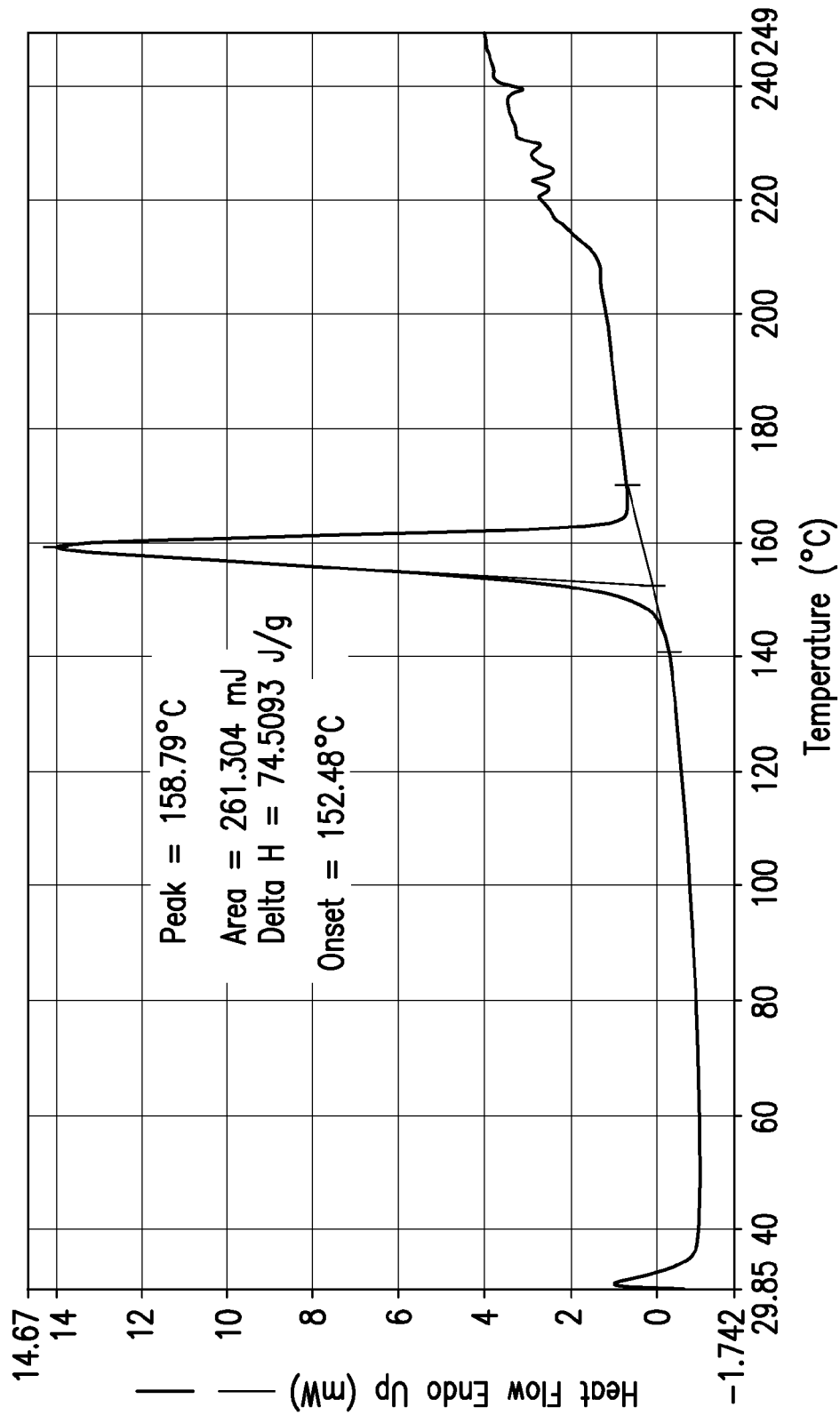
FIG. 5 shows the differential scanning calorimetry (DSC) trace of Form A (Example 1, 2) and was recorded on a Perkin Elmer Diamond DSC instrument with aluminium pan (Perkin Elmer, type BO14-3018); heating rate 20 K/min, temperature range: 30 to 250° C.

FIG. 5 shows the DSC trace of Form A. Melting endotherm: $T_{onset}$=152.5° C., ΔH=74.5 J/g.

c) Infrared spectroscopy:

FIG. 3 shows an infrared spectrum of Form A (Example 3) and was recorded on a Bruker Alpha instrument in attenuated total reflection (ATR) mode. Measurement parameters were as follows: range 400-4000 cm$^{-1}$, resolution 2 cm$^{-1}$, 64 scans, velocity 7.5 kHz, apodisation: Blackman-Harris 3-term. Major peaks identified are 1621.5 cm$^{-1}$, 1157.5 cm$^{-1}$ and 1080.7 cm$^{-1}$.

Figure 6:
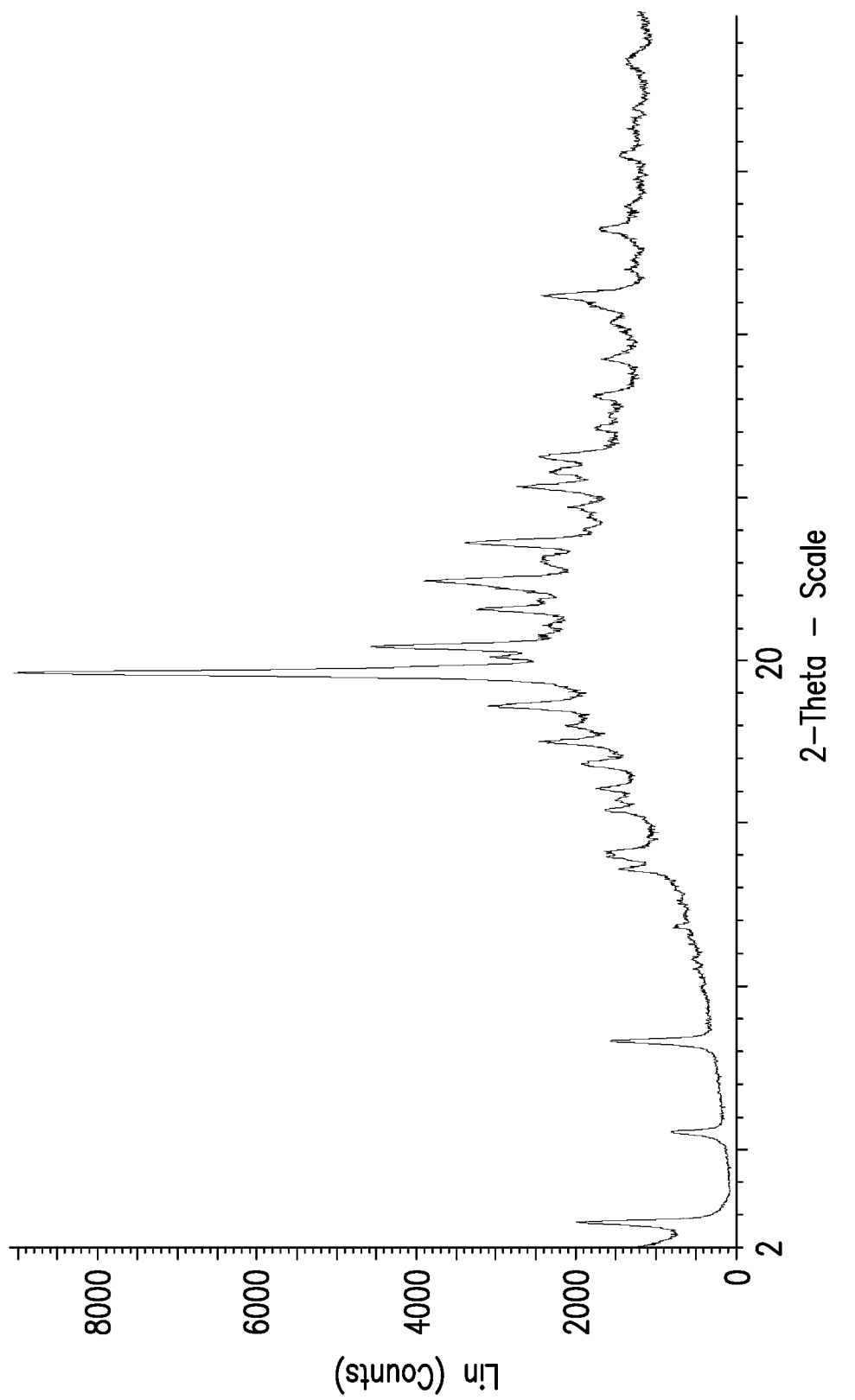
FIG. 6 shows the x-ray powder diffraction pattern recorded for Form B (Example 4, 5, 6, 7) and was recorded on a Bruker™ D8 diffractometer using CuKα radiation (λ=1.5418 Å).

Form B:

X-Ray Powder Diffraction:

An x-ray powder diffraction pattern was recorded on a Bruker™ D8 diffractometer using CuKα radiation (λ=1.5418 Å). The X-ray diffraction pattern thus determined is shown in FIG. 6 and represented in Table 4 below by the reflection lines of the most important lines. The error limit for the 2-Theta angles is ±0.2°.

TABLE 4

| Angle [2-Theta°] | d value [Angstrom] |
|---|---|
| 2.8 | 32.09854 |
| 8.3 | 10.59553 |
| 13.6 | 6.49500 |
| 14.2 | 6.23951 |
| 15.5 | 5.72854 |
| 15.7 | 5.63078 |
| 16.1 | 5.50272 |
| 16.9 | 5.24177 |
| 17.6 | 5.04506 |
| 18.0 | 4.92061 |
| 18.7 | 4.73737 |
| 19.7 | 4.50303 |
| 20.2 | 4.40277 |
| 20.5 | 4.33829 |
| 21.2 | 4.18182 |
| 21.6 | 4.10919 |
| 22.5 | 3.94329 |
| 23.2 | 3.83322 |
| 23.7 | 3.75003 |
| 24.8 | 3.58412 |

TABLE 4-continued

| Angle [2-Theta°] | d value [Angstrom] |
|---|---|
| 25.4 | 3.50000 |
| 25.8 | 3.44564 |
| 26.4 | 3.37345 |
| 27.3 | 3.26453 |
| 28.2 | 3.16479 |
| 31.0 | 2.88279 |
| 31.3 | 2.85617 |
| 33.3 | 2.68916 |

Form C:

a) X-ray powder diffraction:

a1) An x-ray powder diffraction pattern was recorded on a Bruker™ D8 diffractometer using CuKα radiation (λ=1.5418 Å). The X-ray diffraction pattern thus determined is shown in FIG. 7 and represented in Table 5 below by the reflection lines of the most important lines. The error limit for the 2-Theta angles is ±0.2°.

TABLE 5

Figure 10:
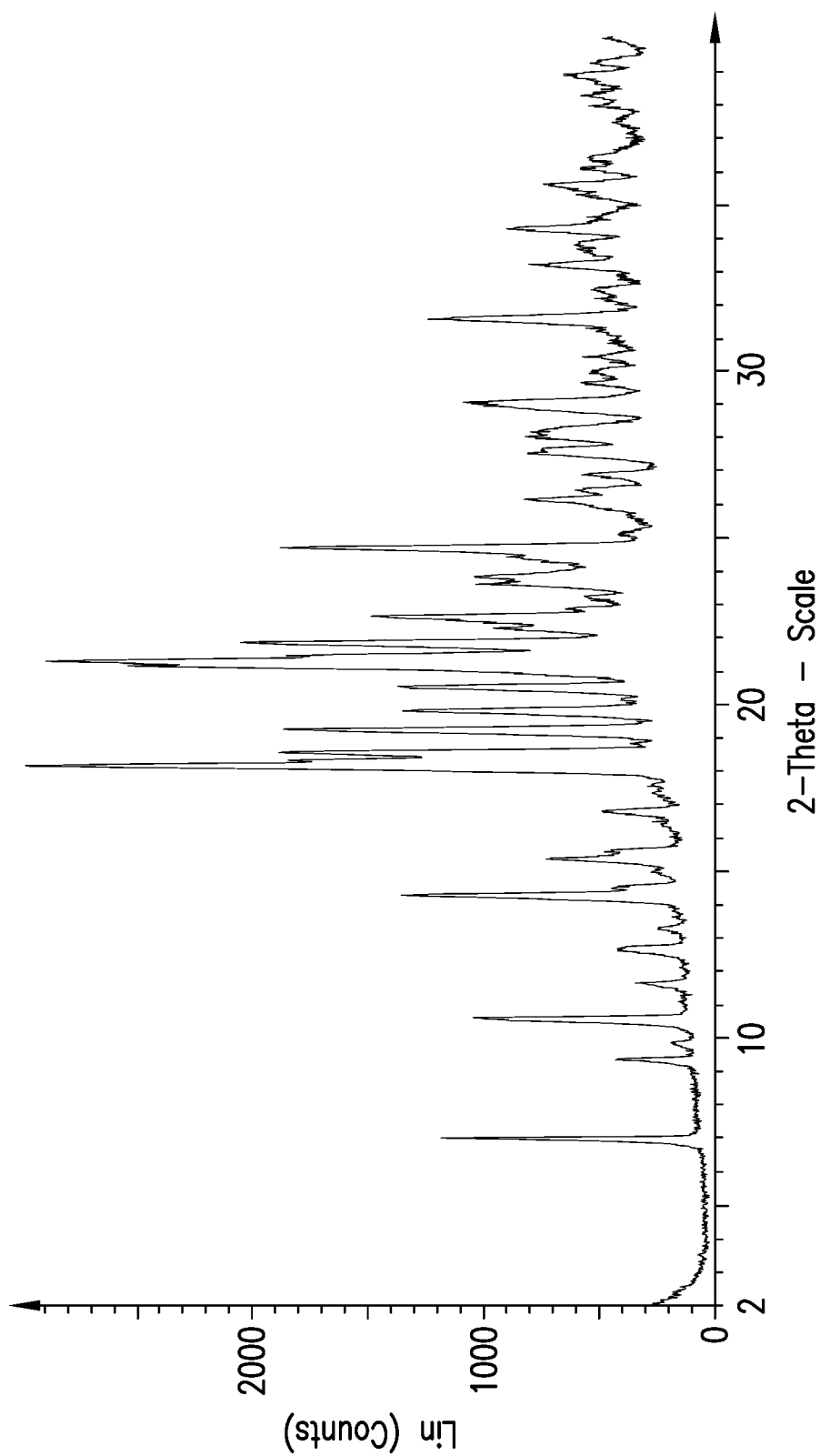
FIG. 10 shows the x-ray powder diffraction pattern recorded for Form C (Example 8, 9) and was recorded on a Bruker™ D8 diffractometer using CuKα radiation (λ=1.5418 Å).

| Angle [2-Theta°] | d value [Angstrom] | Intensity % |
|---|---|---|
| 3.4 | 25.63821 | 16 |
| 7.0 | 12.69761 | 61 |
| 9.3 | 9.45442 | 17 |
| 10.6 | 8.36462 | 45 |
| 12.7 | 6.97632 | 15 |
| 14.3 | 6.20119 | 39 |
| 14.5 | 6.10371 | 11 |
| 15.4 | 5.76664 | 26 |
| 15.6 | 5.68512 | 14 |
| 16.8 | 5.27680 | 19 |
| 18.2 | 4.88346 | 100 |
| 18.6 | 4.77927 | 67 |
| 19.2 | 4.61365 | 67 |
| 19.8 | 4.47997 | 49 |
| 20.5 | 4.32842 | 49 |
| 21.2 | 4.19093 | 79 |
| 21.8 | 4.06888 | 72 |
| 22.3 | 3.99197 | 30 |
| 22.6 | 3.93139 | 41 |
| 23.2 | 3.83169 | 18 |
| 23.6 | 3.76768 | 32 |
| 23.8 | 3.73715 | 26 |
| 24.4 | 3.64553 | 32 |
| 24.7 | 3.60619 | 75 |
| 26.1 | 3.40836 | 29 |
| 26.4 | 3.37439 | 23 |
| 26.9 | 3.31671 | 18 |
| 27.6 | 3.22842 | 25 |
| 28.1 | 3.16770 | 26 |
| 29.0 | 3.07492 | 31 |
| 29.6 | 3.01427 | 19 |
| 30.0 | 2.98012 | 15 |
| 30.4 | 2.93806 | 15 |
| 30.8 | 2.89914 | 13 |
| 31.2 | 2.86666 | 15 |
| 31.5 | 2.83584 | 38 |
| 32.2 | 2.78121 | 15 |
| 32.4 | 2.75849 | 16 |
| 33.1 | 2.70052 | 26 |
| 33.8 | 2.64895 | 19 |
| 34.2 | 2.61820 | 29 | a2) An x-ray powder diffraction pattern was recorded on a Bruker™ D8 diffractometer using CuKα radiation (λ=1.5418 Å). The X-ray diffraction pattern thus determined for Example 8 or 9 is shown in FIG. 10 and represented in Table 6 below by the reflection lines of the most important lines. The error limit for the 2-Theta angles is ±0.2°.

TABLE 6

| Angle [2-Theta°] | d value [Angstrom] |
|---|---|
| 7.0 | 12.64950 |
| 9.4 | 9.44289 |
| 10.6 | 8.35316 |
| 12.7 | 6.98042 |
| 14.3 | 6.19896 |
| 14.5 | 6.08572 |
| 15.0 | 5.91215 |
| 15.4 | 5.76129 |
| 15.6 | 5.68308 |
| 16.8 | 5.27666 |
| 18.2 | 4.88072 |
| 18.5 | 4.78186 |
| 19.2 | 4.61134 |
| 19.8 | 4.48061 |
| 20.5 | 4.32621 |
| 21.3 | 4.17380 |
| 21.8 | 4.06826 |
| 22.3 | 3.99094 |
| 22.6 | 3.93062 |
| 23.2 | 3.83089 |
| 23.6 | 3.76587 |
| 23.8 | 3.73401 |
| 24.4 | 3.65154 |
| 24.7 | 3.60556 |
| 25.1 | 3.54637 |
| 26.1 | 3.40771 |
| 26.4 | 3.37293 |
| 26.9 | 3.31662 |
| 27.5 | 3.23528 |
| 28.1 | 3.17371 |
| 29.0 | 3.07575 |
| 29.6 | 3.01577 |
| 30.0 | 2.98083 |
| 30.4 | 2.93867 |
| 30.8 | 2.89669 |
| 31.2 | 2.86750 |
| 31.5 | 2.83511 |
| 32.1 | 2.78434 |
| 32.4 | 2.76064 |
| 33.1 | 2.70033 |
| 33.8 | 2.65117 |
| 34.2 | 2.61749 |

The temperature in the laboratory during recording of the XRPD data varied between 21 and 26° C.

b) Differential scanning calorimetry (DSC):

DSC traces were recorded on a Perkin Elmer Diamond DSC instrument with aluminium pan (Perkin Elmer, type BO14-3018); heating rate 20 K/min, temperature range: 30 to 250° C.

FIG. 8 shows the DSC trace of Form C (Example 10). Melting endotherm: $T_{onset}$=165.7° C., ΔH=102.2 J/g.

Figure 9:
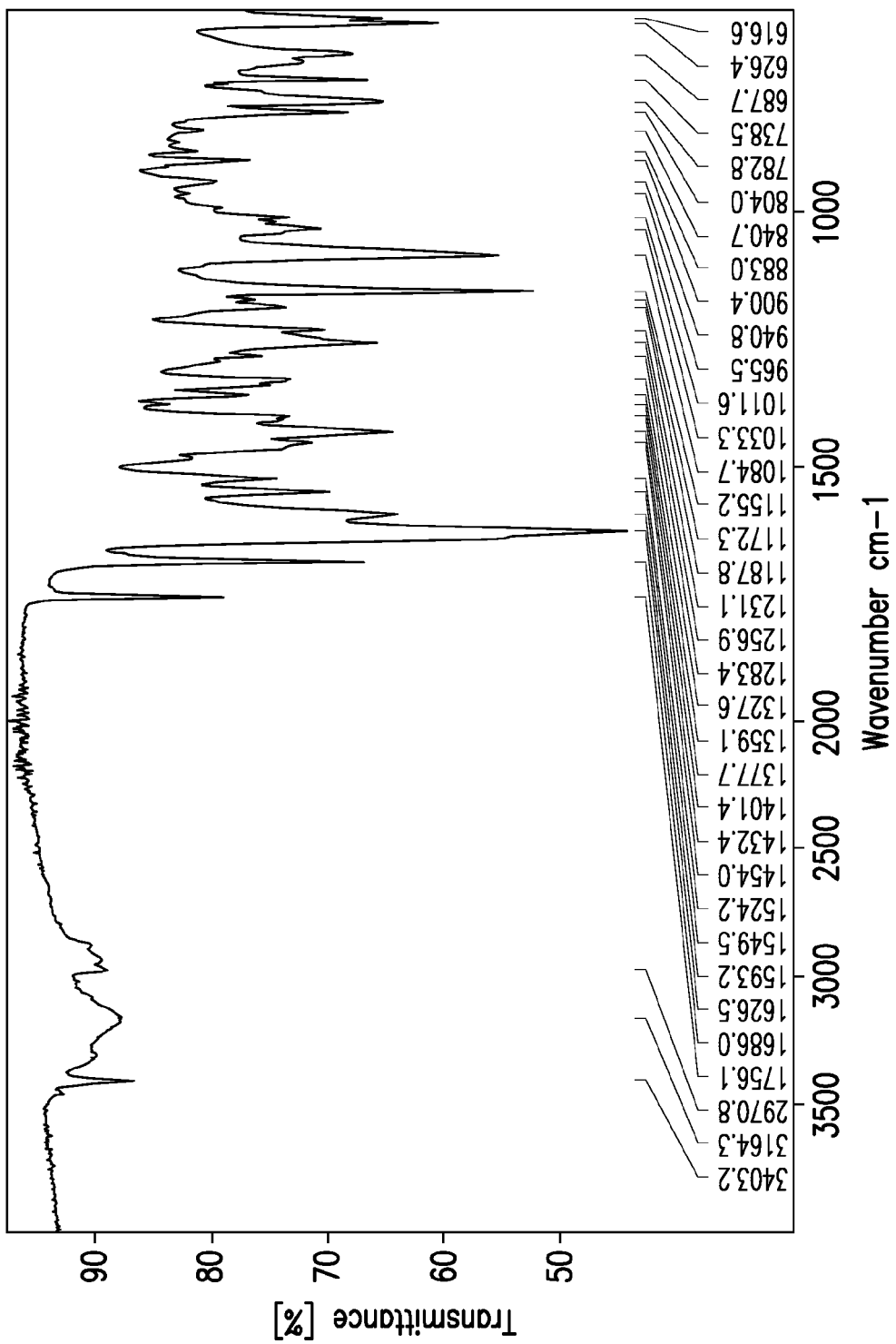
FIG. 9 shows an infrared spectrum of Form C (Example 10) and was recorded on a Bruker Alpha instrument in attenuated total reflection (ATR) mode. Measurement parameters were as follows: range 400-4000 cm$^{-1}$, resolution 2 cm$^{-1}$, 64 scans, velocity 7.5 kHz, apodisation: Blackman-Harris 3-term.
Figure 11:
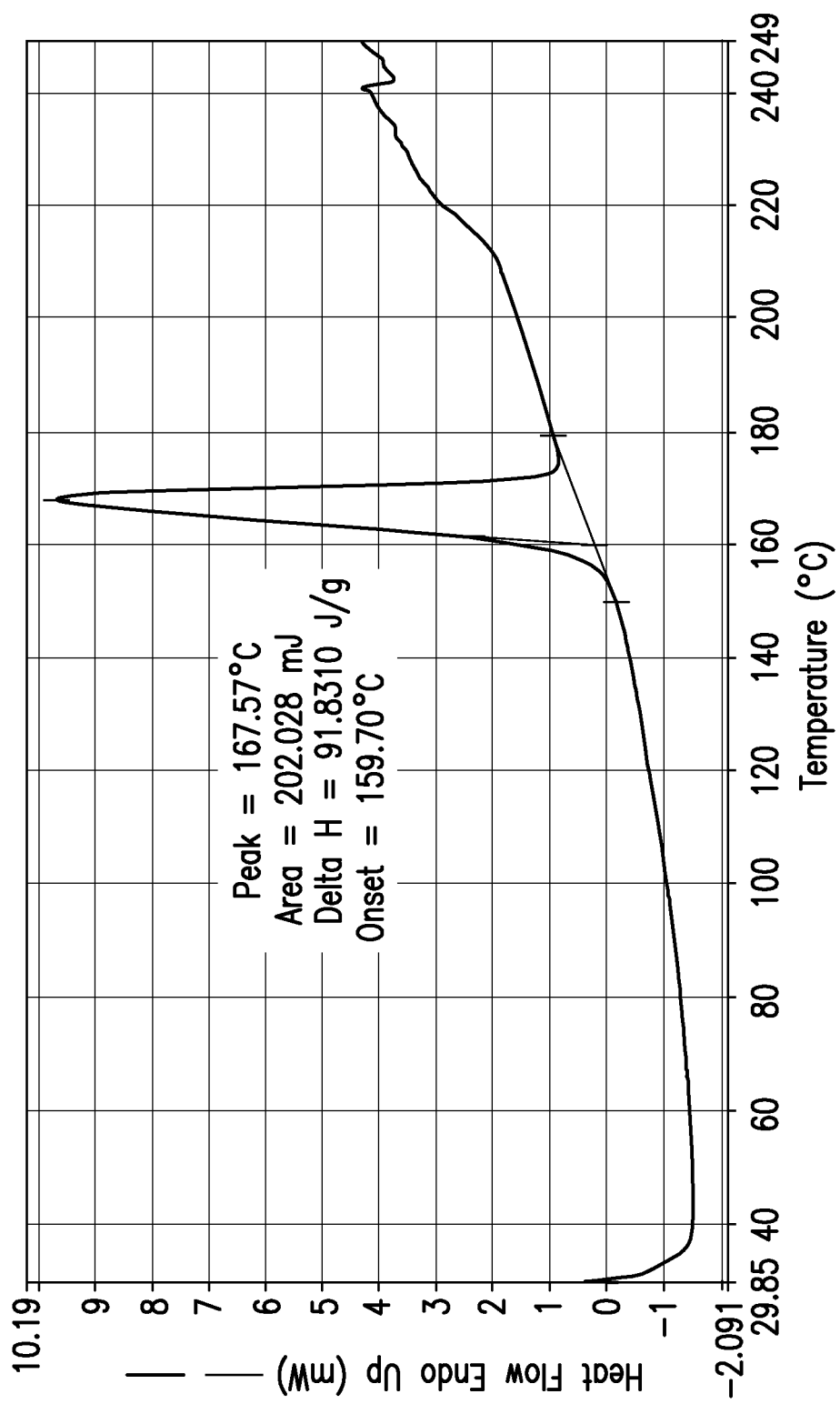
FIG. 11 shows the DSC trace of Form C (Example 8, 9) and was recorded on a Perkin Elmer Diamond DSC instrument with aluminium pan (Perkin Elmer, type BO14-3018); heating rate 20 K/min, temperature range: 30 to 250° C.

FIG. 11 shows the DSC trace of Form C (Example 8, 9). Melting endotherm: $T_{onset}$=159.7° C., ΔH=91.8 J/g.

c) Infrared spectroscopy:

FIG. 9 shows an infrared spectrum of Form C (Example 10) and was recorded on a Bruker Alpha instrument in attenuated total reflection (ATR) mode. Measurement parameters were as follows: range 400-4000 cm$^{-1}$, resolution 2 cm$^{-1}$, 64 scans, velocity 7.5 kHz, apodisation: Blackman-Harris 3-term. Major peaks identified are 1626.5 cm$^{-1}$, 1155 cm$^{-1}$ and 1084.7 cm$^{-1}$.

The invention claimed is:

1. A crystalline form of 3-(3-{2-[(E)-3,5-Diamino-6-chloro-pyrazine-2-carbonylimino]-1,3,8-triaza-spiro[4.5]decane-8-carbonyl}-benzenesulfonylamino)-propionic acid dipropylcarbamoylmethyl ester succinate of formula

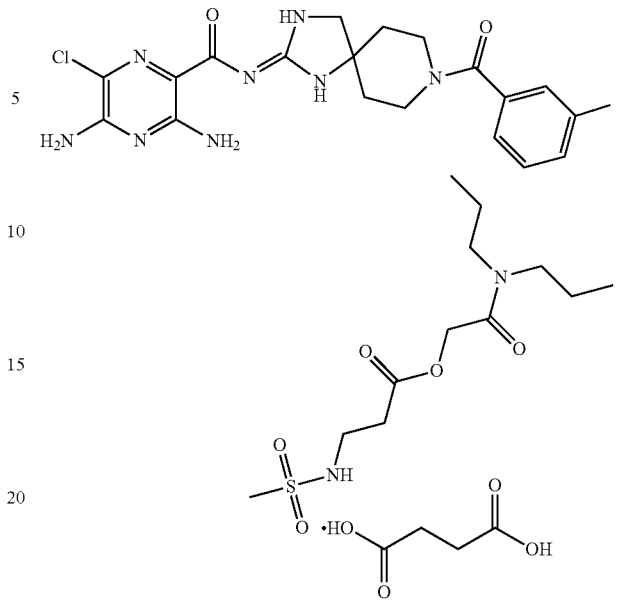

comprising Form C which is characterized by an x-ray powder diffraction pattern, comprising:
four or more 2-theta values selected from the group of 7.0°±0.2, 10.6°±0.2, 14.3°±0.2, 18.2°±0.2, 18.6°±0.2, 19.2°±0.2, 21.2°±0.2, 21.8°±0.2, 24.7°±0.2, 29.0°±0.2 and 31.5°±0.2 at a temperature of 21-26° C.

2. The crystalline form according to claim 1 consisting essentially of Form C.

3. The crystalline form according to claim 1, wherein said Form C is in substantially pure form.

4. The crystalline form according to claim 1, characterized by an x-ray powder diffraction pattern, comprising:
six or more 2-theta values selected from the group of 7.0°±0.2, 10.6°±0.2, 14.3°±0.2, 18.2°±0.2, 18.6°±0.2, 19.2°±0.2, 21.2°±0.2, 21.8°±0.2, 24.7°±0.2, 29.0°±0.2 and 31.5°±0.2 at a temperature of 21-26° C.

5. The crystalline form according to claim 1, wherein the x-ray powder diffraction spectrum is substantially the same as the x-ray powder diffraction spectrum shown in FIG. 7.

6. The crystalline form according to claim 1, wherein the differential scanning calorimetry thermogram is substantially the same as that shown in FIG. 8.

7. A pharmaceutical composition, comprising:
the crystalline form according to claim 1 and
a pharmaceutically acceptable carrier or diluent.

8. The pharmaceutical composition according to claim 7 further comprising one or more additional active ingredients.

9. The pharmaceutical composition according to claim 7, which is in inhalable form.

10. A method of treating respiratory diseases, said diseases selected from the group consisting of cystic fibrosis, primary ciliary dyskinesia, chronic bronchitis, chronic obstructive pulmonary disease (COPD), asthma, respiratory tract infections and lung carcinoma, comprising:
administering to a patient in need thereof an effective amount of the crystalline form according to claim 1.

11. The method according to claim 10, wherein the disease is selected from cystic fibrosis and COPD.

12. The method according to claim 10, wherein the disease is cystic fibrosis.

13. An inhalation device that contains and is adapted to deliver the crystalline form according to claim 1 by pulmonary administration.

* * * * *

UNITED STATES PATENT AND TRADEMARK OFFICE
CERTIFICATE OF CORRECTION

PATENT NO. : 8,809,340 B2  Page 1 of 1
APPLICATION NO. : 13/797411
DATED : August 19, 2014
INVENTOR(S) : Catherine Howsham et al.

It is certified that error appears in the above-identified patent and that said Letters Patent is hereby corrected as shown below:

In the Claims

Column 26, the formula spanning from lines 1-24, that formula reading:

" 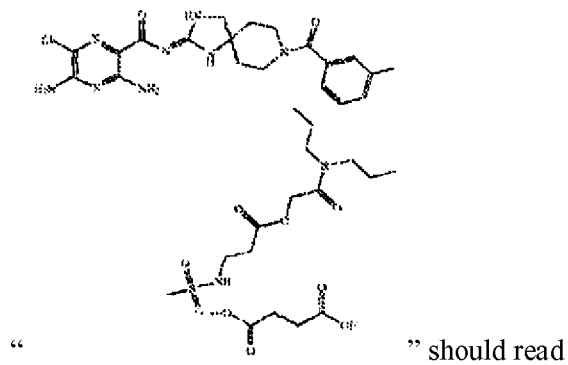 " should read

-- 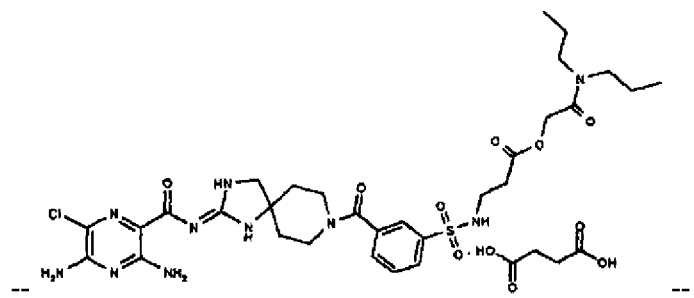 --

Signed and Sealed this
Second Day of June, 2015

Michelle K. Lee
*Director of the United States Patent and Trademark Office*